US006300484B1

(12) United States Patent
Duhl

(10) Patent No.: US 6,300,484 B1
(45) Date of Patent: Oct. 9, 2001

(54) DNA ENCODING DP. 75 AND A PROCESS FOR ITS USE

(75) Inventor: David Duhl, Oakland, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/155,770

(22) PCT Filed: Jun. 4, 1997

(86) PCT No.: PCT/US97/09715

§ 371 Date: Sep. 30, 1998

§ 102(e) Date: Sep. 30, 1998

(87) PCT Pub. No.: WO97/46680

PCT Pub. Date: Dec. 11, 1997

Related U.S. Application Data

(60) Provisional application No. 60/019,180, filed on Jun. 5, 1996.

(51) Int. Cl.$^7$ .................................................. C07H 21/02
(52) U.S. Cl. ............................................................ 536/23.1
(58) Field of Search ............................... 435/6; 536/23.1; 530/350, 300

(56) References Cited

U.S. PATENT DOCUMENTS 5,482,835    1/1996   King et al. .................................. 435/6

FOREIGN PATENT DOCUMENTS

WO 92/10571 * 6/1992 (WO).
WO97/46680   12/1997 (WO).

OTHER PUBLICATIONS

Chiu et al., "Cloning and Characterization of T–Cell Lymphoma Invasion and Metastasis 2 (TIAM2), a Novel Guanine Nucleotide Exchange Factor Related to TIAMI," *Genomics* 61:66–73, 1999.
Hoshino et al., "Identification of the stef Gene That Encodes a Novel Guanine Nucleotide Exchange Factor Specific for Rac1 *," *The Journal of Biological Chemistry* 274 (25):17837–17844, Jun. 18, 1999.
Leeuwen et al., "The Guanine Nucleotide Exchange Factor Tiam 1 Affects Neuronal Morphology; Opposing Roles for the Small GTPases Rac and Rho," *The Journal of Cell Biology* 139 (3):797–807, Nov. 3, 1997.
GenBank Accession No. AB022915, "Identification of the stef gene that encodes a novel guanine nucleotide exchange factor specific for Rac1," Jun. 30, 1999, located at http://www.ncbi.nlm.nih.gov.

Boguski and McCormick, "Proteins regulating Ras and its relatives," *Nature* 366:643–654, 1993.
Chan et al., "Expression cDNA cloning of a novel oncogene with sequence similarity to regulators of small GTP–binding proteins," *Oncogene* 9(4):1057–1063, 1994.
Fantl et al., "Signalling By Receptor Tyrosine Kinases," *Annu. Rev. Biochem.* 62:453–481, 1993.
Habets et al., "Identification of an Invasion–Inducing Gene, Tiam–1, That Encodes a Protein with Homology to GDP–GTP Exchangers for Rho–Like Proteins," *Cell* 77:537–549, 1994.
Habets et al., "Sequence of the human invasion–inducing Tiami gene, its conservation in evolution and its expression in tumor cell lines of different tissue origin," *Oncogene* 10(7) : 1371–1376, 1995.
Hart et al., "Cellular Transformation and Guanine Nucleotide Exchange Activity Are Catalyzed by a Common Domain on the dbl Oncogene Product," *The Journal of Biological Chemistry* 269(1) :62–65, 1994.
Hillier et al., EMBL Sequence Database Accession No. W21217, May 8, 1996.
Horii et al., "A novel oncogene, ost, encodes a guanine nucleotide exchange factor that potentially links Rho and Rac signaling pathways," *The EMBO Journal* 13 (20): 4776–4786, 1994.
Michiels et al., "A role for Rac in Tiam 1–induced membrane ruffling and invasion," *Nature* 375:338–340, 1995.
Miki et al., "Oncogene ect2 is related to regulators of small GTP–binding proteins," *Nature* 362:462–465, 1993.
Ron et al., "Molecular cloning and characterization of the human dbl proto–oncogene: evidence that its overexpression is sufficient to transform NIH/3T3 cells," *The EMBO Journal* 7 (8): 2465–2473, 1988.
Toksoz and Williams, "Novel human oncogene lbc detected by transfection with distinct homology regions to signal transduction products," *Oncogene* 9(2): 621–628, 1994.

* cited by examiner

*Primary Examiner*—Robert A. Schwartzman
*Assistant Examiner*—Mary M. Schmidt
(74) *Attorney, Agent, or Firm*—Jane E. R. Potter; Kimberlin L. Morley; Robert P. Blackburn

(57) ABSTRACT

The present invention is a novel nucleic acid sequence which hybridizes to SEQ ID NO:6 or fragments thereof under stringent conditions, or fragments thereof. The invention also includes diagnostic assays, expression vectors, control sequences, antisense molecule, ribozymes, and host cells to express the polypeptide encoded by the nucleic acid sequence. The present invention also includes claims to the polypeptide sequence coded by the nucleic acid sequences.

1 Claim, 2 Drawing Sheets

SEQUENCE LISTING

<160> NUMBER OF SEQ ID NOS: 7

<210> SEQ ID NO 1
<211> LENGTH: 355
<212> TYPE: DNA
<213> ORGANISM: Homo sapien

<400> SEQUENCE: 1

```
aaggcctttg ttgggtgccc ggaacccac  caagcagcat tcctcacgct ggagtcctac      60
ctcatcaagc cggttcagag agcgctcagg tacccgctgc tgctcaagga gctggtgtcc     120
ctgacggacc aggagagcga ggagcactac cacctgacgg aagcactaaa ggcaatggag     180
aaagtagcga gccacatcaa tgagatgcag aagatctatg aggattatgg gaccgtgttt     240
gaccagctag tagctgagca gagcggaaca gagaaggagg taacagaact ttcgatggga     300
gagcttctga tgcactctac ggtttcctgg ttgaacccaa tgttgatccc cgggg          355
```

<210> SEQ ID NO 2
<211> LENGTH: 19
<212> TYPE: DNA
<213> ORGANISM: Artificial Sequence
<220> FEATURE:
<223> OTHER INFORMATION: Nucleic Acid probe for isolation of DP-75

<400> SEQUENCE: 2

```
aaggcctttg ttgggtgcc                                                   19
```

<210> SEQ ID NO 3
<211> LENGTH: 19
<212> TYPE: DNA
<213> ORGANISM: Artificial Sequence
<220> FEATURE:
<221> NAME/KEY: misc_feature
<222> LOCATION: (1)...(19)
<223> OTHER INFORMATION: n = A,T,C or G
<223> OTHER INFORMATION: Nucleic Acid probe for isolation of DP-75

<400> SEQUENCE: 3
aaggcctttg ytggnyncc                                              19

<210> SEQ ID NO 4
<211> LENGTH: 22
<212> TYPE: DNA
<213> ORGANISM: Artificial Sequence
<220> FEATURE:
<223> OTHER INFORMATION: Nucleic Acid probe for isolation of DP-75

<400> SEQUENCE: 4
ccccggggat caacattggg tt                                          22

<210> SEQ ID NO 5
<211> LENGTH: 22
<212> TYPE: DNA
<213> ORGANISM: Artificial Sequence
<220> FEATURE:
<223> OTHER INFORMATION: Nucleic Acid probe for isolation of DP-75

<400> SEQUENCE: 5
ccccggggat vadvaddggr tt                                          22

<210> SEQ ID NO 6
<211> LENGTH: 2089
<212> TYPE: DNA
<213> ORGANISM: Homo sapien

<400> SEQUENCE: 6
gaattccact tagatgtgat ccgttctccc agagggagca ggtttctttg aacttttcct    60
ttttatgtac agcatagtgc tgagcagatc actgcactgt gcaggagttt taacgacagt   120
caggccaacg gcatggaagg accgcgggag aatcaggatc ctcctccgag gcctctggcc   180
cgccacctgt ctgatgcaga ccgcctccgc aaagtcatcc aggagcttgt ggacacagag   240
aagtcctacg tgaaggattt gagctgcctc tttgaattat acttggagcc acttcagaat   300 gagcctttc ttacccaaga tgagatggag tcacttttttg gaagtttgcc agagatgctt   360
gagtttcaga aggtgtttct ggagaccctg gaggatggga tttcagcatc atctgacttt   420 aacacccctag aaaccccctc acagtttaga aaattactgt tttcccttgg aggctctttc   480
ctttattacg cggaccactt taaactgtac agtggattct gtgctaacca tatcaaagta   540
cagaaggttc tggagcgagc taaaactgac aaagccttca aggcttttct ggacgcccgg   600
aaccccacca gcagcattc ctccacgctg gagtcctacc tcatcaagcc ggttcagaga   660
gtgctcaagt acccgctgct gctcaaggag ctggtgtccc tgacggacca ggagagcgag   720
gagcactacc acctgacgga agcactaaag gcatggagaa agtagcgag ccacatcaat   780 gagatgcaga agatctatga ggattatggg accgtgtttg accagctagt agctgagcag   840
agcggaacag agaaggaggt aacagaactt cgatgggag agcttctgat gcactctacg   900
gtttcctggt tgaatccatt tctgtctcta ggaaaagcta gaaaggacct tgagctcaca   960

-continued

```
gtatttgttt taagagagc cgtcatactg gtttataaag aaaactgcaa actgaaaaag    1020
aaattgccct cgaattcccg gcctgcacac aactctactg acttggaccc atttaaattc    1080
cgctggttga tccccatctc cgcgcttcaa gtcagactgg ggaatccagc agggacagaa    1140
aataattcca tatgggaact gatccatacg aagtcagaaa tagaaggacg ccagaaacc    1200 atctttcagt tgtgttgcag tgacagtgaa agcaaaacca acattgttaa ggtgattcgt    1260
tctattctga gggagaactt caggcgtcac ataaagtgtg aattaccact ggagaaaacg    1320
tgtaaggatc gcctggtacc tcttaagaac cgagttcctg tttcggccaa attagcttca    1380
tccaggtctt taaaagtcct gaagaattcc tccagcaacg agtggaccgg tgagactggc    1440
aagggaacct tgctggactc tgacgagggc agcttgagca gcggcaccca gagcagcggc    1500
tgccccacgg ctgagggcag gcaggactcc aagagcactt ctcccgggaa atacccacac    1560
cccggcttgg cagattttgc tgacaatctc atcaaagaga gtgacatcct gagcgatgaa    1620
gatgatgacc accgtcagac tgtgaagcag ggcagcccta ctaaagacat cgaaattcag    1680
ttccagagac tgaggatttc cgaggaccca gacgttcacc ccgaggctga gcagcagcct    1740
ggcccggagt cgggtgaggg tcagaaagga ggagagcagc ccaaactggt ccgggggcac    1800
ttctgcccca ttaaacgaaa agccaacagc accaagaggg acagaggaac tttgctcaag    1860
gcgcagatcc gtcaccagtc ccttgacagt cagtctgaaa atgccaccat cgacctaaat    1920
tctgttctag agcgagaatt cagtgtccag agtttaacat ctgttgtcag tgaggagtgt    1980
ttttatgaaa cagagagcca cggaaaatca tagtatgatt caatccagat atgggttaaa    2040
ttcctcattt tactttaa ctggtggtaa agtggaaatt gcggaattc                  2089
```

<210> SEQ ID NO 7
<211> LENGTH: 626
<212> TYPE: PRT
<213> ORGANISM: Homo sapien

<400> SEQUENCE: 7

```
Met Glu Gly Pro Arg Glu Asn Gln Asp Pro Pro Arg Pro Leu Ala
 1               5                  10                  15

Arg His Leu Ser Asp Ala Asp Arg Leu Arg Lys Val Ile Gln Glu Leu
                20                  25                  30

Val Asp Thr Glu Lys Ser Tyr Val Lys Asp Leu Ser Cys Leu Phe Glu
            35                  40                  45

Leu Tyr Leu Glu Pro Leu Gln Asn Glu Thr Phe Leu Thr Gln Asp Glu
        50                  55                  60

Met Glu Ser Leu Phe Gly Ser Leu Pro Glu Met Leu Glu Phe Gln Lys
65                  70                  75                  80

Val Phe Leu Glu Thr Leu Glu Asp Gly Ile Ser Ala Ser Ser Asp Phe
                85                  90                  95

Asn Thr Leu Glu Thr Pro Ser Gln Phe Arg Lys Leu Leu Phe Ser Leu
            100                 105                 110

Gly Gly Ser Phe Leu Tyr Tyr Ala Asp His Phe Lys Leu Tyr Ser Gly
        115                 120                 125

Phe Cys Ala Asn His Ile Lys Val Gln Lys Val Leu Glu Arg Ala Lys
    130                 135                 140

Thr Asp Lys Ala Phe Lys Ala Phe Leu Asp Ala Arg Asn Pro Thr Lys
145                 150                 155                 160

Gln His Ser Ser Thr Leu Glu Ser Tyr Leu Ile Lys Pro Val Gln Arg
                165                 170                 175
```

-continued

```
Val Leu Lys Tyr Pro Leu Leu Lys Glu Leu Val Ser Leu Thr Asp
            180                 185                 190

Gln Glu Ser Glu Glu His Tyr His Leu Thr Glu Ala Leu Lys Ala Met
            195                 200                 205

Glu Lys Val Ala Ser His Ile Asn Glu Met Gln Lys Ile Tyr Glu Asp
            210                 215                 220

Tyr Gly Thr Val Phe Asp Gln Leu Val Ala Glu Gln Ser Gly Thr Glu
225                 230                 235                 240

Lys Glu Val Thr Glu Leu Ser Met Gly Glu Leu Leu Met His Ser Thr
                245                 250                 255

Val Ser Trp Leu Asn Pro Phe Leu Ser Leu Gly Lys Ala Arg Lys Asp
                260                 265                 270

Leu Glu Leu Thr Val Phe Val Phe Lys Arg Ala Val Ile Leu Val Tyr
            275                 280                 285

Lys Glu Asn Cys Lys Leu Lys Lys Leu Pro Ser Asn Ser Arg Pro
            290                 295                 300

Ala His Asn Ser Thr Asp Leu Asp Pro Phe Lys Phe Arg Trp Leu Ile
305                 310                 315                 320

Pro Ile Ser Ala Leu Gln Val Arg Leu Gly Asn Pro Ala Gly Thr Glu
                325                 330                 335

Asn Asn Ser Ile Trp Glu Leu Ile His Thr Lys Ser Glu Ile Glu Gly
                340                 345                 350

Arg Pro Glu Thr Ile Phe Gln Leu Cys Cys Ser Asp Ser Glu Ser Lys
            355                 360                 365

Thr Asn Ile Val Lys Val Ile Arg Ser Ile Leu Arg Glu Asn Phe Arg
            370                 375                 380

Arg His Ile Lys Cys Glu Leu Pro Leu Glu Lys Thr Cys Lys Asp Arg
385                 390                 395                 400

Leu Val Pro Leu Lys Asn Arg Val Pro Val Ser Ala Lys Leu Ala Ser
                405                 410                 415

Ser Arg Ser Leu Lys Val Leu Lys Asn Ser Ser Ser Asn Glu Trp Thr
            420                 425                 430

Gly Glu Thr Gly Lys Gly Thr Leu Leu Asp Ser Asp Glu Gly Ser Leu
            435                 440                 445

Ser Ser Gly Thr Gln Ser Ser Gly Cys Pro Thr Ala Glu Gly Arg Gln
            450                 455                 460

Asp Ser Lys Ser Thr Ser Pro Gly Lys Tyr Pro His Pro Gly Leu Ala
465                 470                 475                 480

Asp Phe Ala Asp Asn Leu Ile Lys Glu Ser Asp Ile Leu Ser Asp Glu
                485                 490                 495

Asp Asp Asp His Arg Gln Thr Val Lys Gln Gly Ser Pro Thr Lys Asp
            500                 505                 510

Ile Glu Ile Gln Phe Gln Arg Leu Arg Ile Ser Glu Asp Pro Asp Val
            515                 520                 525

His Pro Glu Ala Glu Gln Pro Gly Pro Glu Ser Glu Gly Gln
            530                 535                 540

Lys Gly Gly Glu Gln Pro Lys Leu Val Arg Gly His Phe Cys Pro Ile
545                 550                 555                 560

Lys Arg Lys Ala Asn Ser Thr Lys Arg Asp Arg Gly Thr Leu Leu Lys
                565                 570                 575

Ala Gln Ile Arg His Gln Ser Leu Asp Ser Gln Ser Glu Asn Ala Thr
            580                 585                 590

Ile Asp Leu Asn Ser Val Leu Glu Arg Glu Phe Ser Val Gln Ser Leu
```

-continued

```
            595                 600                 605
Thr Ser Val Val Ser Glu Glu Cys Phe Tyr Glu Thr Glu Ser His Gly
    610                 615                 620
Lys Ser
625
```

DNA ENCODING DP. 75 AND A PROCESS FOR ITS USE

This application claims the benefit of U.S. Provisional Application No. 60/019,180, filed Jun. 5, 1996, and is the National Stage of International Application No. PCT/US97/09715, filed Jun. 4, 1997.

FIELD OF THE INVENTION

The present invention is in the field of molecular biology. More specifically, the present invention relates to a DNA sequence and corresponding protein.

BACKGROUND OF THE INVENTION

A family of GTP binding proteins and related proteins has been implicated in tumorgenicity of hyperproliferative cells. These proteins include dbl, eci2, lbc, ost, and TIM. See, respectively, Ron et al., *EMBO J* 7: 2465–2473 (1988); Miki el al., *Nature* 362: 462–465 (1993); Toksoz et al., *Oncogene* 9(2): 641–628 (1994); Horii et al., *EMBO J* 13(20): 4776–4786 (1994); Chan et al., *Oncogene* 9(4) 1057–1063 (1994). Also, included in this family is the Tiam-1 protein. This protein has been shown to modulate the invasive potential of a cell. See Habets et al., *Cell* 77: 537–549 (1994); Habets et al., *Oncogene* 10(7): 1371–1376 (1995); and Gaston et al., *Nature* 375: 338–340 (1995). Tiam-1 also has been identified as a member of a family of GDP dissociation stimulators (GDSs). These proteins activate Rho4like and Rac-like GTPases.

SUMMARY

The present invention is a novel nucleic acid sequence which hybridizes to the DP-75 sequence of SEQ ID NO:6 or fragments thereof under stringent conditions. The invention also includes diagnostic assays, expression vectors, control sequences, antisense molecules, ribozymes, and host cells to express the polypeptide encoded by the nucleic acid sequence. The present invention also includes claims to the polypeptide sequence coded by the nucleic acid sequences.

The present invention is also related to pharmaceutical compositions comprising at least one 15- to 40-mer antisense oligonucleotide which is complementary to a region in DP-75; and a pharmaceutically acceptable carrier. The invention is also related to a method for treating cancer by suppressing cancer cell growth using a molecule that can inhibit DP-75, one example is by administering a growth suppressing amount of a DP-75 antisense oligonucleotide.

DETAILED DESCRIPTION OF THE INVENTION

Figure 1:
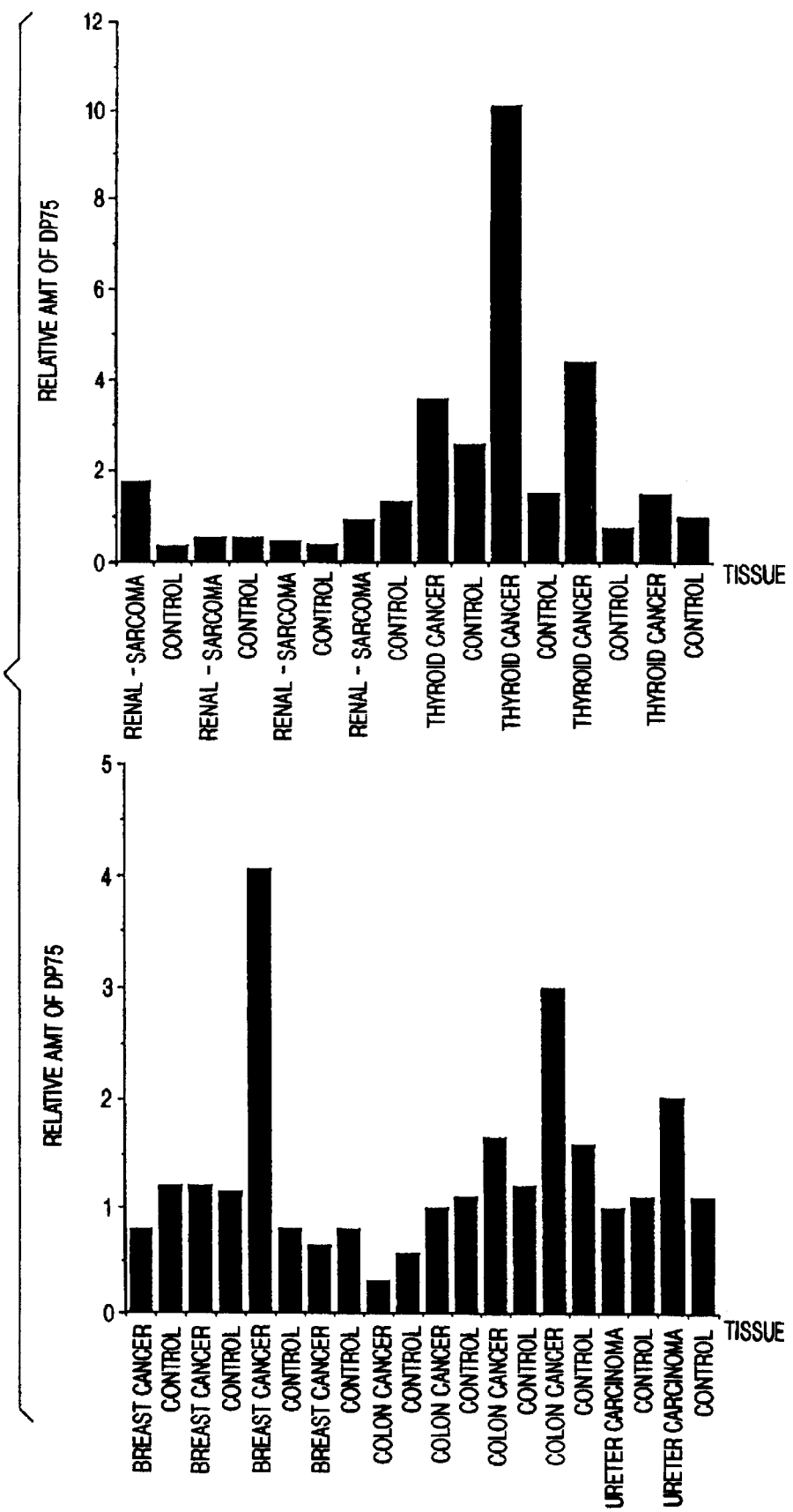
FIG. 1 show the results of a dot blot assay, where DP-75 was hybridized to RNA from both cancerous and normal tissue. The source of cancerous tissue include renal thyroid, breast, colon, and ureter.
Figure 2:
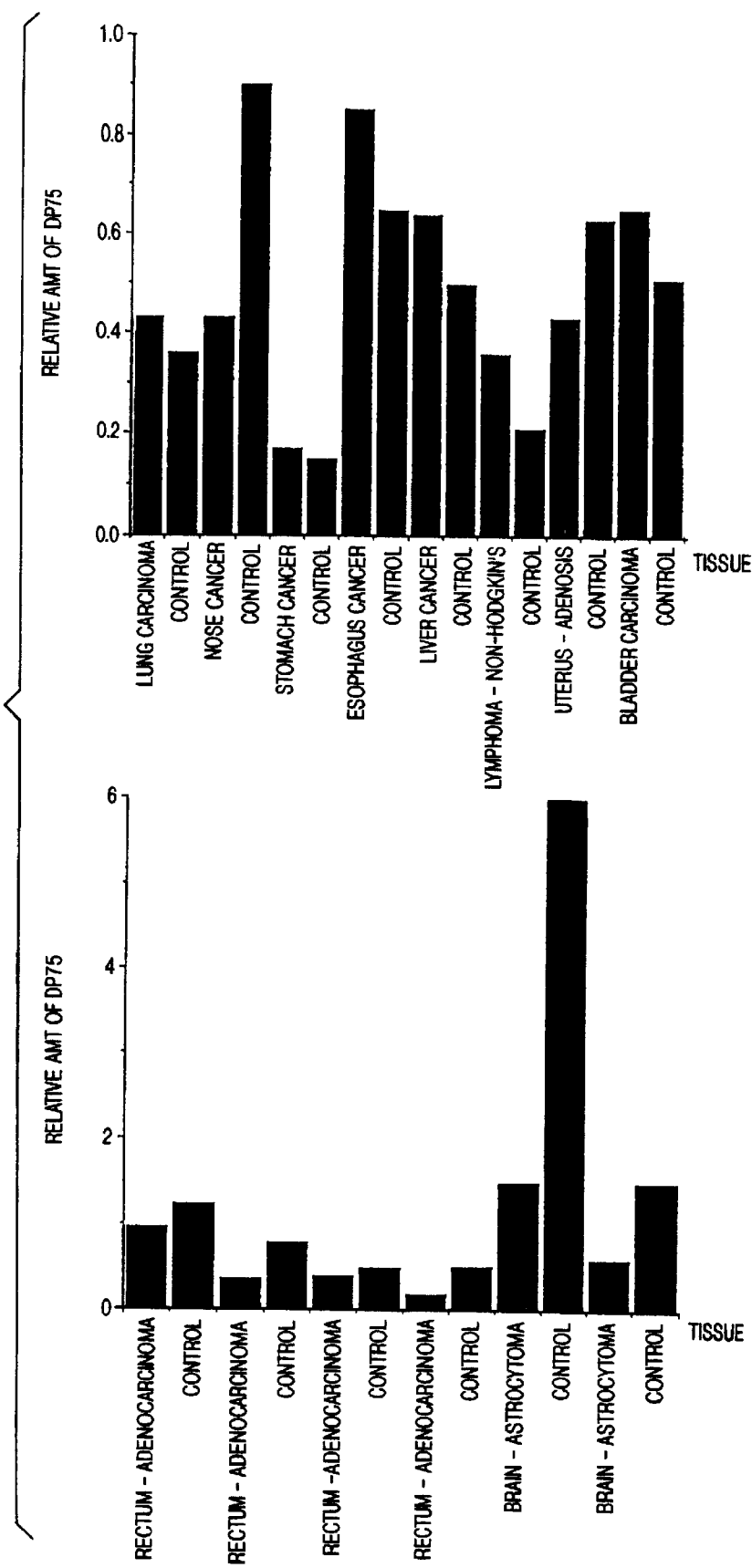
FIG. 2 shows the results of a dot blot assay, where DP-75 was hybridized to RNA from both cancerous and normal tissue. The source of cancerous tissue include lung, nose, stomach, esophagus, liver, lymphoma, uterus, bladder, rectum, and brain.

The practice of the present invention will employ, unless otherwise indicated, conventional techniques of molecular biology, microbiology, and recombinant DNA technology that are within the skill of the art. Such techniques are explained fully in the literature. See e.g., Sambrook, el al., MOLECULAR CLONING; A LABORATORY MANUAL, SECOND EDITION (1989); DNA CLONING, VOLUMES I AND B (D. N Glover ed. 1985); OLIGONUCLEOTIDE SYNTHESIS (M. J. Gait ed, 1984); NUCLEIC ACID HYBRIDIZATION (B. D. Names & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Veriag, N.Y.), HANDBOOK OF EXPERIMENTAL IMMUNOLOGY, VOLUMES I-IV (D. M. Weir and C. C. Blackwell eds 1986); and VACCINES (R. W. Ellis, ed., 1992, Butterworth-Heinemann, London).

Standard abbreviations for nucleotides and amino acids are used in this specification. All publications, patents, and patent applications cited herein are incorporated by reference.

Definitions

"Homology" refers to the degree of similarity between x and y. The correspondence between the sequence from one form to another can be determined by techniques known in the art. For example, they can be determined by a direct comparison of the sequence information of the polynucleotide. Typically, two sequences, either polynucleotide or polypeptide, are homologous if the sequences exhibit at least 45% sequence identity; more typically, 50% sequence identity; more typically, 55% sequence identity; more typically, 60% sequence identity; more typically, 65% sequence identity; even more typically, 70% sequence identity. Usually, two sequences are homologous if the sequences exhibit at least 75% sequence identity; more usually, 80% sequence identity; even more usually, 85% sequence identity; even more usually, 90% sequence identity; and even more usually, 95% sequence identity.

Alternatively, homology can be determined by hybridization of the polynucleotides under conditions which form stable duplexes between homologous regions. Stable duplexes are those, for example, which would withstand digestion with a single-stranded specific nuclease(s), such as $S_1$. Such duplexes can be analyzed by various methods, such as size determination of digested fragments.

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al., MOLECULAR CLONING; A LABORATORY MANUAL, SECOND EDMON (1989), Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 12° to 20° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook, et al., above at page 9.50.

Variables to consider when performing, for example, a Southern blot are (1) the complexity of the DNA being blotted and (2) the homology between the probe and the sequences being detected. The total amount of the fragment (s) to be studied can vary a magnitude of 10, from 0.1 to 1 μg for a plasmid or phage digest to 10-9 to 10-8 μg for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 μg of yeast DNA, blotting for two hours, and hybridizing for 4–8 hours with a probe of $10^8$ cpm/μg. For a single-copy mammalian gene a conservative approach would start with 10 μg of DNA, blot overnight, and hybridize overnight in the presence of 10% dextran sulfate using a probe of greater than $10^8$ cpm/μg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log 10C_i)+0.4[\%G+C)]-0.6(\%\text{formamide})-600/n-1.5(\%\text{mismatch}).$$

where $C_i$ is the salt concentration (monovalentions) and n is the length of the hybrid in base pairs (slightly modified from Meinkoth and Wahl, (1984) Anal. Biochem. 138: 267–284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology and between the probe and the target fragment are not known, the simplest approach is to start with both hybridization and wash conditions which are nonstringent. If nonspecific bands or high background are observed after autoradiography, the filter can be washed at high stringency and reexposed. If the time required for exposure makes this approach impractical, several hybridization and/or washing stringencies should be tested in parallel.

Native DP-75 polypeptide and polynucleotides refer to the proteins and nucleic acids that occur in nature. The amino acid sequence of native polypeptide will comprise a sequence that varies slightly; typically, less than by 10–20 amino acids encoded from SEQ ID NO: 6 or SEQ ID NO:1.

A "vector" or "plasmid" is a nucleic acid sequence in which another polynucleotide segment is attached, so as to bring about the replication and/or expression of the attached segment.

"PCR" refers to the technique of polymerase chain reaction as described in Saiki, et al., Nature 324:163 (1986); and Scharf et al., Science (1986) 233:1076–1078; and U.S. Pat. Nos. 4,683,195; and 4,683,202.

"Control sequence" refers to polynucleotide sequences which facilitate the expression of coding sequences to which they are ligated. The nature of such control sequences differs depending upon the host organism; in eukaryotes, generally, such control sequences include, for example, promoters and transcription termination sequence. The term "control sequences" is intended to include, at a minimum, all components whose presence is facilitate expression, such as the reactions involved in transcription and translation, for instance. The control sequence may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence so that expression of the coding sequence is achieved under conditions compatible with the control sequences.

The term "polynucleotide" or "nucleic acid sequence" as used herein refers to a polymer of nucleotides of any length, preferably deoxyribonucleotides, and is used interchangeably herein with the terms "oligonucleotide" and "oligomer." The term refers only to the primary structure of the molecule. Thus, this term includes double- and single-stranded DNA, as well as antisense polynucleotides. It also includes known types of modifications, for example, the presence of labels which are known in the art, methylation, end "caps," substitution of one or more of the naturally occurring nucleotides with an analog, internucleotide modifications such as, for example, replacement with certain types of uncharged linkages (e.g., methyl phosphonates, phosphotriesters, phosphoamidates, carbamates, etc.) or charged linkages (e.g., phosphorothioates, phosphorodithioates, etc.), introduction of pendant moieties, such as, for example, proteins (including nucleases, toxins, antibodies, signal peptides, poly-L-lysine, etc.), intercalators (e.g., acridine, psoralen, etc.), chelators (e.g., metals, radioactive species, boron, oxidative moieties, etc.), alkylators (e.g., alpha anomeric nucleic acids, etc.).

By "genomic" is meant a collection or library of DNA molecules which correspond to the sequence found in chromosomal DNA as opposed to spliced mRNA. By "cDNA" is meant a DNA sequence that hybridizes to a complimentary strand of mRNA.

As used herein, x is "heterologous" with respect to y if x is not naturally associated with y in the identical manner; i.e., x is not associated with y in nature or x is not associated with y in the same manner as is found in nature.

As used herein, the term "protein" or "polypeptide" refers to a polymer of amino acids and does not refer to a specific length of the product; thus, peptides, oligopeptides, polypeptide, proteins, and polyproteins, as well as fragments of these, are included within this definition. This term also does not refer to, or exclude, post expression modifications of the protein, for example, glycosylations, acetylations, phosphorylations and the like. Included within the definition are, for example, proteins containing one or more analogs of an amino acid (including, for example, unnatural amino acids, etc.), proteins with substituted linkages, as well as other modifications known in the art, both naturally occurring and non-naturally occurring.

A polypeptide or protein or amino acid sequence "derived from" or "coded by" or "encoded by" a designated nucleic acid sequence refers to a polypeptide having an amino acid sequence identical to that of a polypeptide encoded in the sequence, or a portion thereof wherein the portion consists of at least 3–5 consecutive amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation.

"Cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells.

As used herein, the term microorganism" includes prokaryotic and eukaryotic microbial species such as bacteria and fingi, the latter including yeast and filamentous fungi.

"Transformation", as used herein, refers to the insertion of an exogenous polynucleotide into a host cell, irrespective of the method used for the insertion, for example, direct uptake, particle mediated, transduction, f-mating or electroporation. The exogenous polynucleotide may be maintained as a non-integrated vector, for example, a plasmid, or alternatively, may be integrated into the host genome. Examples of particle mediated transduction are shown in U.S. Pat. Nos. 4,945,050 and 5,149,655, which are hereby incorporated by reference in their entireties.

"Purified" and "isolated" mean, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

"Growth suppressing amount" of DP-75 antisense oligonucleotide, for example, refers to an amount of a therapeutic agent to treat, ameliorate, or prevent cancer. The amount is sufficient to exhibit a detectable therapeutic or preventative effect. The effect may include, for example, reduction in growth of abnormal cells, such as cancerous cells; death of cancerous cells; or reduction in the presence of cancer antigens or markers. Therapeutic effects also include reduction of physical displays or symptoms in patients. The precise effective amount for a subject will depend upon the subject's size and health, the nature and extent of the cardiovascular condition, and the therapeutics or combination of therapeutics selected for administration. Thus, it is not useful to specify an exact effective amount in advance. However, the effective amount for a given situation can be determined by routine experimentation and is within the judgment of the clinician.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

General Method

DP-75 is a novel DNA and amino acid sequence that has some sequence homology to other sequences that have been identified with certain cancers. For example, the present DP-75 nucleic acid sequence is partially homologous to a nucleic sequence identified as Tiam-1, see Habets et al., *Cell* 77:537–749(1994), and Habets et al, *Oncogene* 10:1371–1376 (1995) both of which are hereby incorporated by reference in their entireties. Overexpression of full length, or truncated forms of Tiam-1 increases the metastatic potential of lymphoma cells in mice. Tiam-1 is a member of a family GDP dissociation stimulators (GDSs) which are proteins that activate Rho-like and Rac-like GTPases. GDSs as well as Rho and Rac have oncogenic potential.

To assay for the ability of DP-75 to induce cellular invasiveness, the method outlined in Habets et al., *Cell* 77:537–749 (1994) can be followed. For example, cells can be transformed with DP-75 and the clones can be administered to experimental animals, i.e. nude mice. See pages 537 and 538 of Habets et al.

It is contemplated that the DP-75 DNA sequence, or its complement, will be usefull in diagnostic assays, expression vectors, control sequences, antisense molecules, ribozymes, and host cells to express the polypeptide encoded by the nucleic acid sequence. The DP-75 amino acid sequence can be used in an assay to screen for inhibitors (preferably small molecules) of DP-75's ability to facilitate GDP-GTP exchange. See Michiels, el al. *Nature,* 375:338–340 (1995) for an appropriate assay. Michiels et al is hereby incorporated by reference in its entirety. For example, this assay could involve the use of DP-75 protein which could be incubated with Rho or Rac along which was loaded with tritiated GDP. DP-75 should release the GDP unless a compound inhibits that release. This inhibition could be measured in the same manner as Michiel et aL DP-75 has been found to be expressed in normal heart, brain, and skeletal muscle, as shown below. The message size was mostly 3 Kb for brain tissue, and appeared to be 6 Kb in heart and skeletal muscle tissue. A more complete look at tissues from different regions of the brain showed that the cerbral cortex, occipital pole, frontal lobe, temporal lobe and putamen contained a 3 Kb message, but that the cerebellum contained a 7.7 Kb message. Accordingly, it appears that there may be differentially spliced versions of DP-75 in various tissues of the body.

DP-75 has some homology to Tiam-1, a protein implicated as a modulator of the invasiveness of tumor cells. Tiam-1 is a GDP dissociation stimulator (GDS). It is a cytosolic protein that affects the invasiveness of T lymphoma cells and it shares domains (Dbl-homologous and Pleckstrin-homologous) with proteins that modulate the activity of rho-like and rac-like proteins. Such rho- and rac-like proteins have been implicated in signal transduction pathways regulating cytoskeletal structures. Further, GDSs modulate the activity of small GTPase molecules that are important in cellular signaling, regulation, secretion, size, shape, adhesion, motility and growth, among other activities A molecule that is a paradigm for these small GTPases is ras, which has been studied extensively and typifies a superfamily of related proteins, such as the rac, rho and rab subfamilies. See Boguski and McConnick, (1993) *Nature,* 366:643–654, which is hereby incorporated by reference in its entirety. See also Fantl et al., *Ann v. Rev. Biochem.* (1993) 62:453–481 for information on signaling by receptor tyrosine kinases, such as p21ras.

Activated ras has been found in about 20% of cancers, and 100% of pancreatic cancers. Ras is normally bound to GTP as an inactive molecule, however, it can be activated when GTP is cleaved to form GDP. These exchange factors typically contain Dbl and Pleckstrin homologous domains that are usefull in cleaving GTP to GDP. It is believed that DP-75 can be important in all of those areas where these regulatory molecules have shown utility.

As stated above, these GDSs are implicated in various cancers and it is believed that DP-75 may be useful to diagnose cancerous cells. Many techniques may be used to diagnose whether tissue samples or people possess DP-75 containing tumor tissue. For example, reverse transcription and PCR amplification of the RNA of a tumor sample to identify the presence of DP-75 mRNA sequences (see Sambrook, et aL, MOLECULAR CLONING; A LABORATORY MANUAL, SECOND EDITION (1989), chapter 14 or Gaugler et al., J. Exp. Med (1994) 179:921–930). Also, immunohistochemical techniques or ELISA assays may be used to identify DP-75 expressing tumors. For example, the DP-75 protein can be recombinantly expressed and then monoclonal antibodies can be prepared according to methods that are known in the art. For example, the methods shown in EP 174,204, Kohler and Milstein, *Nature* (1975) 256:495–497, Fong et al., *J Immun. Meth.* (1984) 70:83–90, GB 2,086,937,2,113,715, EP 57,107, 62,409, EP 118,893, EP 124,301, and EP 131,878 are suited to the present invention. The anti DP-75 monoclonal antibodies can then be used in the standard assays recited above or those assays that are otherwise known in the art.

Monoclonal antibodies may also be used therapeutically. The anti-DP-75 monoclonal antibodies can be administered by means known in the art. Preferably, the antibodies are administered parenterally or subcutaneously, more preferably, they are administered intravenously. The monoclonal antibodies can be administered in combination with other agents designed to promote the activity of the antibodies or to treat the underlying condition involving the DP-75 expressing cell.

Additionally, branched DNA testing may be performed to assay for DP-75 DNA as shown in U.S. Pat. Nos. 5,124,246, and 4,868,105 (hereby incorporated by reference in their entireties). DP-75 nucleic acid probe molecules for the branched DNA testing are preferably from 10 to 50 bases in length, more preferably, between 15 and 40 bases in length, most preferably, between 20 and 30 bases in length.

Ribozymes may be designed to act on the DP-75 sequence identified in SEQ ID NO:6 or fragments thereof. For example, Kashani-Cabet and Scanlon review the state of the art in *Cancer Gene Therapy,* (1995) 2:213–223 (hereby incorporated by reference in its entirety). The authors discuss the biochemistry of the hammerhead and hairpin ribozymes and discuss their role in gene therapy, HIV and cancer.

A ribozyme can be designed to act on the DP-75 sequence to cut it at particular locations. For example, FIG. 1 of KashaniCabet shows the structure of a hammerhead ribozyme and the directions to design these ribozymes against any gene. According to Kashani-Cabet, FIG. 1 shows that there are three helices, and a stem loop structure, as well as the binding area. The authors further disclose methods for intracellular delivery of a ribozyme of interest, using such techniques as naked ribozyme delivery, liposomes, and chemical modifications to the ribozyme.

Kashani-Cabet also discuss hairpin ribozymes which have four helical regions and two loop structures. The authors state that there are essential nucleotide sequences in some of these structures. Additionally, cellular ribozyme expression may be useful to provide the ribozymes to their substrate, without their degradation.

To obtain cellular expression, the ribozyme gene is cloned into an available vector and transfected into the cells of choice. Different vectors may be chosen based on the target cell to be infected. For example, respiratory cells may be targeted by an adeno or adeno associated virus (AAV) vector. Appropriate promoters may be inserted into these vectors to ensure regulatable expression. (see Kashani-Cabet at page 216).

Antisense molecules can be developed based on the DP-75 sequence shown in SEQ ID NO:1 or SEQ ID NO:6. For example, see U.S. Pat. Nos. 5,491,133 and 5,271,941 which are hereby incorporated by reference in their entireties.

Antisense RNA sequences have been described as naturally occurring biological inhibitors of gene expression in both prokaryotes (Mizuno, T., Chou, M–Y, and Inouye, M. (1984), Proc. Natl. Acad. Sci. USA 81, (1966–1970)) and eukaryotes (Heywood, S. M. Nucleic Acids Res., 14, 6771–6772 (1986) and these sequences presumably function by hybridizing to complementary mRNA sequences, resulting in hybridization arrest of translation (Paterson, B. M., Roberts, B. E., and Kuff, E. L., (1977) Proc. Natl. Acad. Sci. USA, 74,4370–4374.

Antisense oligodeoxynucleotides are short synthetic nucleotide sequences formulated to be complementary to a specific gene or RNA message. Through the binding of these oligomers to a target DNA or mRNA sequence, transcription or translation of the gene can be selectively blocked and the disease process generated by that gene can be halted. The cytoplasmic location of mRNA provides a target considered to be readily accessible to antisense oligodeoxynucleotides entering the cell; hence much of the work in the field has focused on RNA as a target.

Currently, the use of antisense oligodeoxynucleotides provides a useful tool for exploring regulation of gene expression in vitro and in tissue culture (Rothenberg, M. et al., (1989) J. Natl. Cancer Inst., 81:1539–1544).

Antisense therapy is the administration of oligonucleotides which bind to a target polynucleotide located within the cells. These oligonucleotides are usually exogenous, but they can be endogenously expressed. The term "antisense" refers to the fact that such oligonucleotides are complementary to their intracellular targets, e.g., DP-75. See for example, Jack Cohen, OLIGODEOXYNUCLEOTIDES, Antisense Inhibitors of Gene Expression, CRC Press, 1989;and Synthesis 1:1–5 (1988).

The DP-75 antisense oligonucleotides of the present invention include derivatives such as S-oligonucleotides (phosphorothioate derivatives or S-oligos, see, Jack Cohen, supra) which exhibit enhanced cancer cell growth inhibitory action. The DP-75 antisense oligonucleotides of the present invention may be RNA or DNA which are complementary to and stably hybridize with the DP-75 genome or the corresponding mRNA. Use of an oligonucleotide complementary to this region allows for the selective hybridization to DP-75 mRNA and not to other mRNAs.

Preferably, the DP-75 antisense oligonucleotides of the present invention are a 15 to 40-mer fragment of the antisense DNA molecule which hybridizes to DP-75 mRNA. Alternatively, the preferred DP-75 antisense oligonucleotide is a 20 to 30-mer oligonucleotide which is complementary to a region in DP-75. Included in the present invention are phamnaceutical compositions comprising an effective amount of at least one of the DP-75 antisense oligonucleotides of the invention in combination with a pharmaceutically acceptable carrier. In one embodiment, a single DP-75 antisense oligonucleotide is utilized. In another embodiment, two DP-75 antisense oligonucleotides are utilized which are complementary to adjacent regions of the DP-75 genome.

Administration of two DP-75 antisense oligonucleotides which are complementary to adjacent regions of the DP-75 genome or corresponding mRNA may allow for more efficient inhibition of DP-75 genomic transcription or mRNA translation, resulting in more effective inhibition of cancer cell growth. Preferably, the DP-75 antisense oligonucleotide is coadministered with an agent which enhances the uptake of the antisense molecule by the cells. For example, the DP-75 antisense oligonucleotide may be combined with a lipophilic cationic compound which may be in the form of liposomes.

The use of liposomes to introduce nucleotides into cells is taught, for example, in U.S. Pat. Nos. 4,897,355 and 4,394,448, the disclosures of which are incorporated by reference in their entireties. See also U.S. Pat. Nos. 4,235,871, 4,231,877, 4,224,179, 4,753,788, 4,673,567, 4,247,411, 4,814,270 for general methods of preparing liposomes comprising biological materials. Alternatively, the DP-75 antisense oligonucleotide may be combined with a lipophilic carrier such as any one of a number of sterols including cholesterol, cholate and deoxycholic acid. A preferred sterol is cholesterol. In addition, the DP-75 antisense oligonucleotide may be conjugated to a peptide that is ingested by cells. Examples of useful peptides include peptide hormones, antigens or antibodies, and peptide toxins. By choosing a peptide that is selectively taken up by the neoplastic cells, specific delivery of the antisense agent may be effected.

The DP-75 antisense oligonucleotide may be covalently bound via the 5' H group by formation of an activated aminoalkyl derivative. The peptide of choice may then be covalently attached to the activated DP-75 antisense oligonucleotide via an amino and sulfhydryl reactive hetero bifimctional reagent. The latter is bound to a cysteine residue present in the peptide. Upon exposure of cells to the DP-75 antisense oligonucleotide bound to the peptide, the peptidyl antisense agent is endocytosed and the DP-75 antisense oligonucleotide binds to the target DP-75 mRNA to inhibit translation. See PCT Application Publication No. PCT/US89/02363.1.

The DP-75 antisense oligonucleotides and the pharmaceutical compositions of the present invention may be administered by any means that achieve their intended purpose. For example, administration of the antisense compounds or other compounds of the present invention may be by parenteral, subcutaneous, intravenous, intramuscular, intra-peritoneal, or transdermal routes.

The dosage administered will be dependent upon the age, health, and weight of the recipient, kind of concurrent treatment, if any, frequency of treatment, and the nature of the effect desired. Compositions within the scope of this invention include all compositions wherein the DP-75 antisense oligonucleotide is contained in an amount which is effective to achieve inhibition of proliferation and/or stimulate differentiation of the subject cancer cells.

While individual needs vary, determination of optimal ranges of effective amounts of each component is within the skill of the art. Typically, the DP-75 antisense oligonucleotide may be administered to mammals, e.g. humans, at a dose of 0.005 to 1 mg/kg/day, or an equivalent amount of the pharmaceutically acceptable salt thereof, per day of the body weight of the mammal being treated.

In addition to administering the DP-75 antisense oligonucleotides as a raw chemical in solution, the DP-75 antisense oligonucleotides may be administered as part of a pharmaceutical preparation containing suitable pharmaceutically acceptable carriers comprising excipients and auxiliaries which facilitate processing of the DP-75 antisense oligonucleotide into preparations which can be used pharmaceutically.

Suitable formulations for parenteral administration include aqueous solutions of the DP-75 antisense oligonucleotides in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The antisense oligonucleotides of the present invention may be prepared according to any of the methods that are well known to those of ordinary skill in the art. Preferably, the antisense oligonucleotides are prepared by solid phase synthesis. See, Goodchild, J., *Bioconjugate Chemistry*, 1: 165–167 (1990), for a review of the chemical synthesis of oligonucleotides. Alternatively, the antisense oligonucleotides can be obtained from a number of companies which specialize in the custom synthesis of oligonucleotides.

One limitation utilizing oligonucleotides as therapeutic agents is the rapid degradation of the oligonucleotide in blood and within cells by nucleases. Such enzymes hydrolyze the phosphodiester bonds joining the nucleotides within a DNA or RNA chain, thereby cleaving the molecule into smaller fragments. In the past, there has been some progress made in the development of oligonucleotide analogs that are resistant to nuclease degradation, but the use of such derivatives to block the expression of specifically targeted genes has met with limited success. See, for example, Ts'o el al. U.S. Pat. No. 4,469,863 issued Sep. 4, 1984; Miller el al. U.S. Pat. No. 4,507,433 issued Mar. 26, 1985; and Miller el al U.S. Pat. No. 4,511,713 issued Apr. 16, 1985, all of the above patents are hereby incorporated by reference in their entireties.

The work described in each of the three prior patents mentioned involves the use of oligonucleotides in which all of the phosphate groups have been modified in the form of methylphosphonates. U.S. Pat. No. 5,491,133 shows that oligonucleotides modified at only the 3'-most internucleotide link are markedly protected from degradation within blood and within cells. Moreover, such derivatives have normal hybridization properties and do form substrates with mRNAs that are recognized and cleaved by RNaseH, thereby preventing expression of the targeted gene. The accomplishment of the inhibition of expression of selected genes by oligonucleotides that are resistant to degradation, and, therefore, more effective when used therapeutically, is another objective of this invention.

It may be useful to administer the nucleic acid molecules described above, i.e. the ribozyme or antisense molecules, in a gene therapy method. Accordingly, the vectors and techniques described below will be useful. The following expression systems describe vectors, promoters and regulatory elements that are usefull for gene therapy applications for the delivery of the above polynucleotides.

Vectors and expression systems useful for the present invention include viral and non-viral systems. Example viral delivery systems include retroviruses, adenoviruses, adeno-associated viruses (AAV), sindbis and herpes viruses. In one aspect of the present invention, the viral vector is capable of integrating the above nucleic acid sequence into the host cell genome for long term expression.

Examples of vectors that can integrate in this fashion are retroviruses and AAV. One preferred retrovirus is a murine leukemia virus. However, it may be preferred to avoid integration into the host cell genome. Non-viral vectors include naked DNA and DNA formulated with cationic lipids or liposomes.

Retroviral vectors are produced by genetically manipulating retroviruses. Retroviral vectors are effective for integration into the host cell genome, as explained above. However, they only infect dividing cells. Retroviral vectors contain RNA and once it enters the cell, it is reverse transcribed into DNA and stably integrated into the host cell genome.

The wild type retrovirus genome contains three genes: the gag, pol, and env genes, which are flanked by the long terminal repeat (LTR) sequences. The gag gene encodes the nucleocapsid proteins, the pol gene encodes the viral enzymes including reverse transcriptase and integrase, the env gene encodes the viral envelope glycoproteins. The 5' and 3' LTRs serve to promote transcription and polyadenylation of virion RNAs. Adjacent to the 5' LTR are sequences necessary for reverse transcription of the genome (the RNA primer binding site) and for efficient encapsulation of viral RNA into particles (the Pi site). See Mulligan, R. C., In: Experimental Manipulation of Gene Expression, M. Inouye (Ed), 155–173 (1983); Mann, R. et al., Cell (1983) 33:153–159; Cone, RD and R. C. Mulligan, Proc. Natl. Acad Sci. (USA), (1984) 81:6349–6353.

Also, AAV are advantageous because they replicate to a high titer, they integrate efficiently, are not pathogenic to humans, are stable, easy to purify, and they infect non-dividing cells. An AAV vector is constructed by inserting the nucleic acid sequence, under the control of a suitable promoter/enhancer, between the AAV LTRs, which are the only sequences required in cis for AAV replication. This DNA construct is transfected into a suitable human cell line in the presence of another plasmid which expresses Rep and CAP, the AAV coding regions needed for replication. At a suitable time post-tansfection, the cells are infected with a helper virus, such as Adenovirus or Herpes Simplex virus. After infection, vector particles are harvested from these cells. The AAV particles are purified from contaminating Adenovirus or Herpes Virus by standard protocols.

Adenovirus is advantageous because it infects a wide variety of cells, infects non-dividing cells, produces a high titer, the biology is well understood, and it can accept large inserts. The adenovirus gene expression is controlled by a cascade of genes. For example, the gene expression order is "immediate early", "early", DNA synthesis, and late or structural genes. These genes are turned on in sequence. The master gene that is turned on first is EIA. One preferred embodiment would involve replacing the EIA gene with the nucleic acid sequence of interest and transfecting this vector into cells that constitutively produce E1A, such as 293 cells which are publicly available. The vector contains all the genes necessary for virion production and the cell line provides the missing E1A protein.

One non-viral system that can be used is the T7/T7 system. Here a short promoter sequence recognized by the bacterial virus T7 polymerase is placed on a vector upstream of the nucleic acid sequence of interest. The vector can then be inserted into cells and the missing T7 polymerase can be added to obtain gene transcription. Alternatively, a vector containing the following sequences can be made, the T7 promoter sequence, the T7 polymerase gene, another copy of the T7 promoter sequence, and the above nucleic acid sequences. In this embodiment, the vector is transformed into cells and simply requires a small amount of T7 polymerase to initiate. Thereafter, the vector directs the manufacture of its own polymerase.

Additionally, it will be useful to produce DP-75 protein from the presently disclosed nucleic acid sequence to be used in an assay to test for inhibitors or for the preparation of monoclonal antibodies, for example. DP-75 can be produced by a prokaryotic microorganism or an euaryotic cell that has been transformed with a native or modified DP-75 nucleic acid sequence. The DP-75 nucleic acid sequence useful in the present invention encodes a protein having an amino acid sequence that is substantially identical to the amino acid sequence of native DP-75.

Preferably, the DP-75 nucleic acid or protein sequence will be homologous to the partial sequences listed below. Preferably, the above sequence will be greater than 95% homologous to SEQ ID NO:6 or figments thereof, more preferably it will be greater than 98% homologous, most preferably greater than 99% homologous. Substantial identity means the sequences are identical or differ by one or more alterations (deletion, additions, substitutions) that do not adversely affect the activity of the protein. It is preferable that the protein sequences are homologous in the same percentages noted above.

The precise chemical structure of the DP-75 sequence depends on a number of factors. As ionizable amino and carboxyl groups are present in the molecule, a particular protein may be obtained as a acidic or basic salt, or in neutral form. All such preparations which retain their activity when placed in suitable environmental conditions are included in the definition of proteins herein. Further, the primary amino acid sequence of the protein may be augmented by derivitization using sugar moieties (glycosylation) or by other supplementary molecules such as lipids, phosphate, acetyl groups and the like. Certain aspects of such augmentation are accomplished through post-translational processing systems of the producing host; other such modifications may be introduced in vitro. In any event, such modifications are included in the definition of protein herein so long as the activity of the protein is not destroyed. It is expected that such modifications may quantitatively or qualitatively affect the activity, either by enhancing or diminishing the activity of the protein, in the various assays. Further, individual amino acid residues in the chain may be modified by oxidation, reduction, or derivatization, and the protein may be cleaved to obtain fragments which retain activity. Such alterations which do not destroy activity do not remove the protein sequence from the definition of DP-75 herein.

Finally, modifications to the primary structure itself, by deletion, addition, or alteration of the amino acids incorporated into the sequence during translation, can be made without destroying the activity of the protein. For example, site specific mutagenesis can enable specific changes in the DNA structure to effect a change in the polypeptide structure. See Mark et al. U.S. Pat. No. 4,959,314, and Sambrook, et al., MOLECULAR CLONING; A LABORATORY MANUAL, SECOND EDITION (1989), Volume 2, chapter 15 which is hereby incorporated by reference in its entirety.

The amino acid sequence of DP-75 proteins can be divided into four general categories: mutants, fragments, fissions, and the protein encoded by the sequence listed in SEQ ID NO:6, SEQ ID NO:1, or fragments thereof and other homologs found in other organisms. The native DP-75 proteins are those that occur in nature. The amino acid sequence of native polypeptide will comprise a sequence that varies slightly; typically, less than by 10–20 amino acids from SEQ ID NO: 6 or SEQ ID NO:1.

A sequence encoding a native DP-75 protein can be easily modified to encode other classes of DP-75 proteins. For example, mutants can be constructed by making conservative amino acid substitutions. The following are examples of conservative substitutions: Gly←→Ala; Val←→Leu; Asp←→Glu; Lys←→Arg; Asn←→Gln; and Phe←→Trp←→Tyr. A subset of mutants, called muteins, is a group of polypeptide with the non-disulfide bond participating cysteines substituted with a neutral amino acid, generally, with serines. These mutants may be stable over a broader temperature range than native DP-75 proteins. Mutants can also contain amino acid deletions or insertions compared to the native DP-75 proteins. The coding sequence of mutants can be constructed by in vitro mutagenesis of the native DP-75 polypeptide coding sequences.

Fragments are amino and/or carboxyl terminal amino acid deletions of mutant or native DP-75 proteins. The number of amino acids that are truncated is not critical as long as the polypeptide fragment exhibits the desired sequence homology, immunological or biological activity. Polypeptide fragments of immunological significance comprise, for example, at least one epitope shared by a native DP-75 protein. Such DP-75 proteins may be only 5–15 amino acids in length. Examples of amino acid sequence of fragments include amino acid number 1–8 (aa1 to aa8) of SEQ ID NO:7; aa2 to aa9 of SEQ ID NO:7; aa3 to aa10 of SEQ ID NO:7; aa4 to aa11 of SEQ ID NO:7; aa5 to aa12 of SEQ ID NO:7; aa6 to aa13 of SEQ ID NO:7; aa7 to aa14 of SEQ ID NO:7; aa8 to aa15 of SEQ ID NO:7; aa9 to aa16 of SEQ ID NO:7; aa10 to aa17 to of SEQ ID NO:7; aa11 to aa18 of SEQ ID NO:7; aa12 to aa19 of SEQ ID NO:7 ; aa13 to aa20 of SEQ ID NO:7; aa14 to aa21 of SEQ ID NO:7 ; aa15 to aa22 of SEQ ID NO:7 ; aa16 to aa23 of SEQ ID NO:7; aa17 to aa24 of SEQ ID NO:7; aa18 to aa25 of SEQ ID NO:7; aa19 to aa26 of SEQ ID NO:7; aa20to aa27 of SEQ ID NO:7; aa to aa28 of SEQ ID NO:7; aa22 to aa29 of SEQ ID NO:7; aa23 to aa30of SEQ ID NO:7; aa24 to aa31 of SEQ ID NO:7; aa25 to aa32 of SEQ ID NO:7; aa26 to a33 of SEQ ID NO:7; aa27 to aa34 of SEQ ID NO:7; aa28 to aa35 of SEQ ID NO:7; aa29 to aa36 of SEQ ID NO:7; aa30 to aa37 of SEQ ID NO:7; aa31 to aa38 of SEQ ID NO:7; aa32 to aa39 of SEQ ID NO:7; aa33 to aa40 of SEQ ID NO:7; aa34 to aa41 of SEQ ID NO:7; aa35 to aa42 of SEQ ID NO: 7; aa36 to aa43 of SEQ ID NO:7; aa37 to aa44 of SEQ ID NO:7; aa38 to aa45 of SEQ ID NO:7; aa39 to aa46 of SEQ ID NO:7; aa40 to aa47 of SEQ ID NO:7; aa41 to aa48 of SEQ ID NO:7; aa42 to aa49 of SEQ ID NO:7; aa43 to aa50 of SEQ ID N0:7; aa44 to aa51 of SEQ ID NO:7; aa45 to aa52 of SEQ ID NO:7; aa46 to aa53 of SEQ ID NO:7; aa47 to aa54 of SEQ ID NO:7; aa48 to aa55 of SEQ ID NO:7; aa49 to aa56 of SEQ ID NO:7; aa50 to aa57 of SEQ ID NO:7; aa51 to aa58 of SEQ ID NO:7; aa52 to aa59 of SEQ ID NO:7; aa53 to aa60of SEQ ID NO:7; aa54 to aa61of SEQ ID NO:7; aa55 to aa62 of SEQ ID NO:7; aa56 to aa63 of SEQ ID NO:7; aa57 to aa64 of SEQ ID NO:7; aa58 to aa65 of SEQ ID NO:7; aa59 to aa66 of SEQ ID NO:7; aa60to aa67 of SEQ ID NO:7; aa61 to aa68 of SEQ ID NO:7; aa62 to aa69 of SEQ ID NO:7; aa63 to aa70of SEQ ID NO:7; aa64 to aa71 of SEQ ID NO:7; aa65 to aa72 of SEQ ID NO:7; aa66 to aa73 of SEQ ID NO:7; aa67 to aa74 of SEQ ID NO:7; aa68 to aa75 of SEQ ID NO:7; aa69 to aa76 of SEQ ID NO:7; aa70 to aa77 of SEQ ID NO:7, aa71 to aa78 of SEQ ID NO:7; aa72 to aa79 of SEQ ID NO:7; aa73 to aa80 of SEQ ID NO:7; aa74 to aa81 of SEQ ID NO:7; aa75 to aa82 of SEQ ID NO:7; aa76 to aa83 of SEQ ID NO:7; aa77 to aa84 of SEQ ID NO:7; aa78 to aa84 of SEQ ID NO:7; aa79 to aa86 of SEQ ID NO:7; aa80 to aa87 of SEQ ID NO:7; aa81 to aa88 of SEQ ID NO:7; aa82 to aa89 of SEQ ID NO:7; aa83 to aa90 of SEQ ID NO:7; aa84 to aa91 of SEQ ID NO:7; aa85 to aa92 of SEQ ID NO:7; aa86 to aa93 of SEQ ID NO:7; aa87 to aa94 of SEQ ID NO:7; aa88 to aa95 of SEQ ID NO:7; aa89 to aa96 of SEQ ID NO:7; aa98 to aa97 of SEQ ID NO:7; aa91 to aa98 of SEQ ID NO:7; aa92 to aa99 of SEQ ID NO:7; aa93 to aa100 of SEQ ID NO:7; aa94 to aa101 of SEQ ID NO:7 ; aa95 to aa102 of SEQ ID NO:7 ; aa96 to aa103 of SEQ ID NO:7; aa97 to aa104 of SEQ ID NO:7; aa98 to aa105 of SEQ ID NO:7; aa99 to aa106 of SEQ ID NO:7; aa100 to aa107 of SEQ ID NO:7 aa101 to aa108 of SEQ ID NO:7 aa102 to aa109 of SEQ I NO:7; aa103 to aa110 of SEQ ID NO:7; aa104 to aa111 of SEQ ID NO:7; aa105 to aa112 of SEQ ID NO:7; aa106to aa113 of SEQ ID NO:7; aa107 to aa114 of SEQ ID NO:7; aa108 to aa115 of SEQ ID NO:7; aa109 to aa116 of SEQ ID NO:7; aa110 to aa117 of SEQ ID NO:7; aa111 to aa118 of SEQ ID NO:7; aa112 to aa119 of SEQ ID NO:7; aa113 to aa120 of SEQ ID NO:7; aa114 to aa121 of SEQ ID NO:7; aa115 to aa122 of SEQ ID NO:7; aa116 to aa123 of SEQ ID NO:7; aa117 to aa124 of SEQ ID NO:7; aa118 to aa125 of SEQ ID NO:7; aa119 to aa126 of SEQ ID NO:7; aa120 to aa127 of SEQ ID NO:7; aa121 to aa128 of SEQ ID NO:7; aa122 to aa129 of SEQ ID NO:7; aa123 to aa130 of SEQ ID NO:7; aa124 to aa131 of SEQ ID NO:7; aa125 to aa132 of SEQ ID NO:7; aa126 to aa133 of SEQ ID NO:7; aa127 to aa134 of SEQ ID NO:7; aa128 to aa135 of SEQ ID NO:7; aa129 to aa136 of SEQ ID NO:7; aa130 to aa137 of SEQ ID NO:7; aa131 to aa138 of SEQ ID NO:7; aa132 to aa139 of SEQ ID NO:7; aa133 to aa140 of SEQ ID NO:7; aa134 to aa141 of SEQ ID NO:7; aa135 to aa142 of SEQ ID NO:7; aa136 to aa143 of SEQ ID NO:7; aa137 to aa144 of SEQ ID NO:7; aa138 to aa145 of SEQ ID NO:7; aa139 to aa146 of SEQ ID NO:7; aa140 to aa147 of SEQ ID NO:7; aa141 to aa148 of SEQ ID NO:7; aa142 to aa149 of SEQ ID NO:7; aa143 to aa150 of SEQ ID NO:7; aa144 to aa151 of SEQ ID NO:7; aa145 to aa152 of SEQ ID NO:7; aa146 to aa153 of SEQ ID NO:7; aa147 to aa154 of SEQ ID NO:7; aa148 to aa155 of SEQ ID NO:7; aa149 to aa156 of SEQ ID NO:7; aa150 to aa157 of SEQ ID NO:7; aa151 to aa158 of SEQ ID NO:7; aa152 to aa159 of SEQ ID NO:7; aa153 to aa160 of SEQ ID NO:7; aa154 to aa161 of SEQ ID NO:7; aa155 to aa162 of SEQ ID NO:7; aa156 to aa163 of SEQ ID NO:7; aa157 to aa164 of SEQ ID NO:7; aa158 to aa165 of SEQ ID NO:7; aa159 to aa166 of SEQ ID NO:7; aa160 to aa167 of SEQ ID NO:7; aa161 to aa168 of SEQ ID NO:7; aa162 to aa169 of SEQ ID NO:7; aa163 to aa170 of SEQ ID NO:7; aa164 to aa171 of SEQ ID NO:7; aa165 to aa172 of SEQ ID NO:7; aa166 to aa173 of SEQ ID NO:7; aa167 to aa174 of SEQ ID NO:7; aa168 to aa175 of SEQ ID NO:7; aa169 to aa176 of SEQ ID NO:7; aa170 to aa177 of SEQ ID NO:7; aa171 to aa178 of SEQ ID NO:7; aa172 to aa179 of SEQ ID NO:7; aa173 to aa180 of SEQ ID NO:7; aa174 to aa181 of SEQ ID NO:7; aa175 to aa182 of SEQ ID NO:7; aa176 to aa183 of SEQ ID NO:7; aa177 to aa184 of SEQ ID NO:7; aa178 to aa185 of SEQ ID NO:7; aa179 to aa186 of SEQ ID NO:7; aa180 to aa187 of SEQ ID NO:7; aa181 to aa188 of SEQ ID NO:7; aa182 to aa189 of SEQ ID NO:7; aa183 to aa190 of SEQ ID NO:7; aa184 to aa191 of SEQ ID NO:7; aa185 to aa192 of SEQ ID NO:7; aa186 to aa193 of SEQ ID NO:7; aa187 to aa194 of SEQ ID NO:7; aa188 to aa195 of SEQ ID NO:7; aa189 to aa196 of SEQ ID NO:7; aa190 to aa197 of SEQ ID NO:7; aa191 to aa198 of SEQ ID NO:7; aa192 to aa199 of SEQ ID NO:7; aa193 to aa200 of SEQ ID NO:7; aa194 to aa201 of SEQ ID NO:7; aa195 to aa202 of SEQ ID NO:7; aa196 to aa203 of SEQ ID NO:7; aa197 to aa204 of SEQ ID NO:7; aa198 to aa205 of SEQ ID NO:7; aa199 to aa206 of SEQ ID NO:7; aa200 to aa207 of SEQ ID NO:7; aa201 to aa208 of SEQ ID NO:7; aa202 to aa209 of SEQ ID NO:7; aa203 to aa210 of SEQ ID NO:7; aa204 to aa211 of SEQ ID NO:7; aa205 to aa212 of SEQ ID NO:7; aa206 to aa213 of SEQ ID NO:7; aa207 to aa214 of SEQ ID NO:7; aa208 to aa215 of SEQ ID NO:7; aa209 to aa216 of SEQ ID NO:7; aa210 to aa217 of SEQ ID NO:7; aa211 to aa218 of SEQ ID NO:7; aa212 to aa219 of SEQ ID NO:7; aa213 to aa220 of SEQ ID NO:7; aa214 to aa221 of SEQ ID NO:7; aa215 to aa222 of SEQ ID NO:7; aa216 to aa223 of SEQ ID NO:7; aa217 to aa224 of SEQ ID NO:7; aa218 to aa225 of SEQ ID NO:7; aa219 to aa226 of SEQ ID NO:7; aa220 to aa227 of SEQ ID NO:7; aa221 to aa228 of SEQ ID NO0:7; aa222 to aa229 of SEQ ID NO:7; aa223 to aa230 of SEQ ID NO:7; aa224 to aa231 of SEQ ID NO:7; aa225 to aa232 of SEQ ID NO:7; and aa226 to aa233; of SEQ ID NO:7 aa227 to aa234 of SEQ ID NO:7; aa228 to aa235 of SEQ ID NO:7; aa229 to aa236 of SEQ ID NO:7; aa230 to aa237 of SEQ ID NO:7; aa231 to aa238 of SEQ ID NO:7; aa222 to aa239 of SEQ ID NO:7; aa233 to aa240 of SEQ ID NO:7; aa234 to aa41 of SEQ ID NO:7; aa235 to aa242 of SEQ ID NO:7; aa236 to aa243 of SEQ ID NO:7; aa237 to aa244 of SEQ ID NO:7; aa238 to aa245 of SEQ ID NO:7; aa239 to aa246 of SEQ ID NO:7; aa240 to aa247 of SEQ ID NO:7; aa241 to aa248 of SEQ ID NO:7; aa242 to aa249 of SEQ ID NO:7; aa243 to aa250 of SEQ ID NO:7; aa244 to aa251 of SEQ ID NO:7; aa245 to aa252 of SEQ ID NO:7; aa246 to aa253 of SEQ ID NO:7; aa247 to aa254 of SEQ ID NO:7; aa248 to aa255 of SEQ ID NO:7; aa249 to aa256 of SEQ ID NO:7; aa250 to aa257 of SEQ ID NO:7; aa251 to aa258 of SEQ ID NO:7; aa252 to aa259 of SEQ ID NO:7; aa253 to aa260 of SEQ ID NO:7; aa254 to aa261 of SEQ ID NO:7; aa255 to aa262 of SEQ ID NO:7; aa256 to aa263 of SEQ ID NO:7; aa257 to aa264 of SEQ ID NO:7; aa258 to aa265 of SEQ ID NO:7; aa259 to aa266 of SEQ ID NO:7; aa260 to aa267 of SEQ ID NO:7; aa261 to aa268 of SEQ ID NO:7; aa262 to aa269 of SEQ ID NO:7; aa263 to aa270 of SEQ ID NO:7; aa264 to aa271 of SEQ ID NO:7; aa265 to aa272 of SEQ ID NO:7; aa266 to aa273 of SEQ ID NO:7; aa267 to aa274 of SEQ ID NO:7; aa268 to aa275 of SEQ ID NO:7; aa269 to aa276 of SEQ ID NO:7; aa270 to aa277 of SEQ ID NO:7; aa271 to aa278 of SEQ ID NO:7; aa272 to aa279 of SEQ ID NO:7; aa273 to aa280 of SEQ ID NO:7; aa274 to aa281 of SEQ ID NO:7; a275 to aa282 of SEQ ID NO:7; aa276 to aa283 of SEQ ID NO:7; aa277 to aa284 of SEQ ID NO:7; aa278 to aa284 of SEQ ID NO:7; aa279 to aa286 of SEQ ID NO:7; aa280 to aa287 of SEQ ID NO:7; aa281 to aa288 of SEQ ID NO:7; aa282 to aa289 of SEQ ID NO:7; aa283 to aa290 of SEQ ID NO:7; aa284 to aa291 of SEQ ID NO:7; aa285 to aa292 of SEQ ID NO:7; aa286 to aa293 of SEQ ID NO:7; aa287 to aa294 of SEQ ID NO:7; aa288 to aa295 of SEQ ID NO:7; aa289 to aa296 of SEQ ID NO:7; aa290 to aa297 of SEQ ID NO:7; aa291 to aa298 of SEQ ID NO:7; aa292 to aa299 of SEQ ID NO:7; aa293 to aa300 of SEQ ID NO:7; aa294 to aa101 of SEQ ID NO:7; aa295 to aa102 of SEQ ID NO:7; aa296 to aa103 of SEQ ID NO:7; aa297 to aa104 of SEQ ID NO:7; aa298 to aa105 of SEQ ID NO:7; aa299 to aa106 of SEQ ID NO:7; aa300 to aa307 of SEQ ID NO:7 aa301 to aa308 of SEQ ID NO:7 aa302 to aa309 of SEQ ID NO:7; aa303 to aa310 of SEQ ID NO:7; aa304 to aa311 of SEQ ID N;O:7; aa305 to aa312 of SEQ ID NO:7; aa306 to aa313 of SEQ ID NO:7; aa307 to aa314 of SEQ ID NO:7; aa308 to aa315 of SEQ ID NO:7; aa309 to aa316 of SEQ ID NO:7; aa310 to aa317 of SEQ ID NO:7 aa311 to aa318 of SEQ ID NO:7; aa312 to aa319 of SEQ ID NO:7; aa313 to aa320 of SEQ ID NO:7; aa314 to aa321 of SEQ ID NO:7; aa315 to aa322 of SEQ ID NO:7; aa316 to aa323 of SEQ ID NO:7; aa317 to aa324 of SEQ ID NO:7; aa318 to aa325 of SEQ ID NO:7; aa319 to aa326 of SEQ ID NO:7; aa320 to aa327 of SEQ ID NO:7; aa321 to aa328 of SEQ ID NO:7; aa322 to aa329 of SEQ ID NO:7; aa323 to aa330 of SEQ ID NO:7; aa324 to aa331 of SEQ ID NO:7; aa325 to aa332 of SEQ ID NO:7; aa326 to aa333 of SEQ ID NO:7; aa327 to aa334 of SEQ ID NO:7; aa328 to aa335 of SEQ ID NO:7; aa329 to aa336 of SEQ ID NO:7; aa330 to aa337 of SEQ ID NO:7; aa331 to aa338 of SEQ ID NO:7; aa332 to aa339 of SEQ ID NO:7; aa333 to aa340 of SEQ ID NO:7; aa334 to aa341 of SEQ ID NO:7; aa335 to aa342 of SEQ ID NO:7; aa336 to aa343 of SEQ ID NO:7; aa337 to aa344 of SEQ ID NO:7; aa338 to aa345 of SEQ ID NO:7; aa339 to aa346 of SEQ ID NO:7; aa340 to aa347 of SEQ ID NO:7; aa341 to aa348 of SEQ ID NO:7; aa342 to aa349 of SEQ ID NO:7; aa343 to aa350 of SEQ ID NO:7; aa344 to aa351 of SEQ ID NO:7; aa345 to aa352 of SEQ ID NO:7; aa346 to aa353 of SEQ ID NO:7; aa347 to aa354 of SEQ ID NO:7; aa348 to aa355 of SEQ ID NO:7; aa349 to aa356 of SEQ ID NO:7; aa350 to aa357 of SEQ ID NO:7; aa351 to aa358 of SEQ ID NO:7; aa352 to aa359 of SEQ ID NO:7; aa353 to aa360 of SEQ ID NO:7; aa354 to aa361 of SEQ ID NO:7; aa355 to aa362 of SEQ ID NO:7; aa356 to aa363 of SEQ ID NO:7; aa357 to aa364 of SEQ ID NO:7; aa358 to aa365 of SEQ ID NO:7; aa359 to aa366 of SEQ ID NO:7; aa360 to aa367 of SEQ ID NO:7; aa361 to aa368 of SEQ ID NO:7; aa362 to aa369 of SEQ ID NO:7; aa363 to aa370 of SEQ ID NO:7; aa364 to aa371 of SEQ ID NO:7; aa365 to aa372 of SEQ ID NO:7; aa366 to aa373 of SEQ ID NO:7; aa367 to aa374 of SEQ ID NO:7; aa368 to aa375 of SEQ ID NO:7; aa369 to aa376 of SEQ ID NO:7; aa370 to aa377 of SEQ ID NO:7; aa371 to aa378 of SEQ ID NO:7; aa372 to aa379 of SEQ ID NO:7; aa373 to aa380 of SEQ ID NO:7; aa374 to aa381 of SEQ ID NO:7; aa375 to aa382 of SEQ ID NO:7; aa376 to aa383 of SEQ ID NO:7; aa377 to aa384 of SEQ ID NO:7; aa378 to aa385 of SEQ ID NO:7; aa379 to aa386 of SEQ ID NO:7; aa380 to aa387 of SEQ ID NO:7; aa381 to aa388 of SEQ ID NO:7; aa382 to aa389 of SEQ ID NO:7; aa383 to aa390 of SEQ ID NO:7; aa384 to aa391 of SEQ ID NO:7; aa385 to aa392 of SEQ ID NO:7; aa386 to aa393 of SEQ ID NO:7; aa387 to aa394 of SEQ ID NO:7; aa388 to aa395 of SEQ ID NO:7; aa389 to aa396 of SEQ ID NO:7; aa390 to aa397 of SEQ ID NO:7; aa391 to aa398 of SEQ ID NO:7; aa392 to aa399 of SEQ ID NO:7; aa393 to aa400 of SEQ ID NO:7; aa394 to aa401 of SEQ ID NO:7; aa395 to aa402 of SEQ ID NO:7; aa396 to aa403 of SEQ ID NO:7; aa397 to aa404 of SEQ ID NO:7; aa398 to aa405 of SEQ ID NO:7; aa399 to aa406 of SEQ ID NO:7; aa400 to aa407 of SEQ ID NO:7; aa401 to aa408 of SEQ ID NO:7; aa402 to aa409 of SEQ ID NO:7; aa403 to aa410 of SEQ ID NO:7; aa404 to aa411 of SEQ ID NO:7; aa405 to aa412 of SEQ ID NO:7; aa406 to aa413 of SEQ ID NO:7; aa407 to aa414 of SEQ ID NO:7; aa408 to aa415 of SEQ ID NO:7; aa409 to aa416 of SEQ ID NO:7; aa410to aa417 of SEQ ID NO:7; aa411 to aa418 of SEQ ID NO:7; aa412 to aa419 of SEQ ID NO:7; aa413 to aa420 of SEQ ID NO:7; aa414 to aa421 of SEQ ID NO:7; aa415 to aa422 of SEQ ID NO:7; aa416 to aa423 of SEQ ID NO:7; aa417 to aa424 of SEQ ID NO:7; aa418 to aa425 of SEQ ID NO:7; aa419 to aa426 of SEQ ID NO:7; aa420 to aa427 of SEQ ID NO:7; aa421 to aa428 of SEQ ID NO:7; aa422 to aa429 of SEQ ID NO:7; aa423 to aa430 of SEQ ID NO:7; aa424 to aa431 of SEQ ID NO:7; aa425 to aa432 of SEQ ID NO:7; aa426 to aa433 of SEQ ID N0:7; aa427 to aa434 of SEQ ID NO:7; aa428 to aa435 of SEQ ID NO:7; aa429 to aa436 of SEQ ID NO:7; aa430 to aa437 of SEQ ID NO:7; aa431 to aa438 of SEQ ID NO:7; aa432 to aa439 of SEQ ID NO:7; aa433 to aa440 of SEQ ID NO:7; aa434 to aa441 of SEQ ID NO:7; aa435 to aa442 of SEQ ID NO:7; aa436 to aa443 of SEQ ID NO:7; aa437 to aa444 of SEQ ID NO:7; aa438 to aa445 of SEQ ID NO:7; aa439 to aa446 of SEQ ID NO:7; aa440 to aa447 of SEQ ID NO :7; aa441 to aa448 of SEQ ID NO:7; aa442 to aa449 of SEQ ID NO:7; aa443 to aa450 of SEQ ID NO:7; aa444 to aa451 of SEQ ID NO:7; aa445 to aa452 of SEQ ID NO:7; aa446 to aa453 of SEQ ID N0:7; aa447 to aa454 of SEQ ID NO:7; aa448 to aa455 of SEQ ID NO:7; aa449 to aa456 of SEQ ID NO:7; aa450 to aa457 of SEQ ID NO:7; aa451 to aa458 of SEQ ID NO:7; aa452 to aa459 of SEQ ID NO:7; aa453 to aa460 of SEQ ID NO:7; aa454 to aa461 of SEQ ID NO:7; aa455 to aa462 of SEQ ID NO:7; aa456 to aa463 of SEQ ID NO:7; aa457 to aa464 of SEQ ID NO:7; aa458 to aa465 of SEQ ID NO:7; aa459 to aa466 of SEQ ID NO:7; aa460 to aa467 of SEQ ID NO:7; aa461 to aa468 of SEQ ID NO:7; aa462 to aa469 of SEQ ID NO:7; aa463 to aa470 of SEQ ID NO:7; aa464 to aa471 of SEQ ID NO:7; aa465 to aa472 of SEQ ID NO:7; aa466 to aa473 of SEQ ID NO:7; aa467 to aa474 of SEQ ID NO:7; aa468 to aa475 of SEQ ID NO:7; aa469 to aa476 of SEQ ID NO:7; aa470 to aa477 of SEQ ID NO:7; aa471 to aa478 of SEQ ID NO:7; aa472 to aa479 of SEQ ID NO:7; aa473 to aa480 of SEQ ID NO:7; aa474 to aa481 of SEQ ID NO:7; aa475 to aa482 of SEQ ID NO:7; aa476 to aa483 of SEQ ID NO:7; aa477 to aa484 of SEQ ID NO:7; aa478 to aa484 of SEQ ID NO:7; aa479 to aa486 of SEQ ID NO:7; aa480 to aa487 of SEQ ID NO:7; aa481 to aa488 of SEQ ID NO:7; aa482 to aa489 of SEQ ID NO:7; aa483 to aa490 of SEQ ID NO:7; aa484 to aa491 of SEQ ID NO:7; aa485 to aa492 of SEQ ID NO:7; aa486 to aa493 of SEQ ID NO:7; aa487 to aa494 of SEQ ID NO:7; aa488 to aa495 of SEQ ID NO:7; aa489 to aa496 of SEQ ID NO:7; aa490 to aa497 of SEQ ID NO:7; aa491 to aa498 of SEQ ID NO:7; aa492 to aa499 of SEQ ID NO:7; aa493 to aa500 of SEQ ID NO:7; aa494 to aa01 of SEQ ID NO:7; aa495 to aa502 of SEQ ID NO:7; aa496 to aa503 of SEQ ID NO:7; aa497 to aa504 of SEQ ID NO:7; aa498 to aa505of SEQ ID NO:7; aa499 to aa506 of SEQ ID NO:7; aa500 to aa507 of SEQ ID NO:7 aa 501 to aa508 of SEQ ID NO:7 aa502 to aa509 of SEQ ID NO:7; aa503 to aa510 of SEQ ID NO:7; aa504to aa511 of SEQ ID NO:7; aa505 to aa512 of SEQ ID NO:7; aa506to aa513 of SEQ ID NO:7; aa507 to aa514 of SEQ ID NO:7; aa508 to aa515 of SEQ ID NO:7; aa509 to aa516 of SEQ ID NO:7; aa510 to aa517 of SEQ ID NO:7; aa511 to aa518 of SEQ ID NO:7; aa512 to aa519 of SEQ ID NO:7; aa513 to aa520 of SEQ ID NO:7; aa514 to aa521 of SEQ ID NO:7; aa515 to aa522 of SEQ ID NO:7; aa516 to aa523 of SEQ ID NO:7; aa517 to aa524 of SEQ ID NO:7; aa518 to aa525 of SEQ ID NO:7; aa519 to aa526 of SEQ ID NO:7; aa520 to aa527 of SEQ ID NO:7; aa521 to aa528 of SEQ ID NO:7; aa522 to aa529 of SEQ ID NO:7; aa523 to aa530 of SEQ ID NO:7; aa524 to aa531 of SEQ ID NO:7; aa525 to aa532 of SEQ ID NO:7; aa526 to aa533 of SEQ ID NO:7; aa527 to aa534 of SEQ ID NO:7; aa528 to aa535 of SEQ ID NO:7; aa529 to aa536 of SEQ ID NO:7; aa530 to aa537 of SEQ ID NO:7; aa531 to a538 of SEQ ID N0:7; aa532 to aa539 of SEQ ID NO:7; aa533 to aa540 of SEQ ID NO: 7; aa534 to aa541 of SEQ ID NO:7; aa535 to aa542 of SEQ ID NO:7; aa536 to aa543 of SEQ ID NO:7; aa537 to aa544 of SEQ ID NO:7; aa538 to aa545 of SEQ ID NO:7; aa539 to aa546 of SEQ ID NO:7; aa540 to aa547 of SEQ ID NO:7; aa541 to aa548 of SEQ ID NO:7; aa542 to aa549 of SEQ ID NO:7; aa543 to aa550 of SEQ ID NO:7; aa544 to aa551 of SEQ ID NO:7; aa545 to aa552 of SEQ ID NO:7; aa546 to aa553 of SEQ ID NO:7; aa547 to aa554 of SEQ ID NO:7; aa548 to aa555 of SEQ ID NO:7; aa549 to aa556 of SEQ ID NO:7; aa550 to aa557 of SEQ ID NO:7; aa551 to aa558 of SEQ ID NO:7; aa552 to aa559 of SEQ ID NO:7; aa553 to aa560 of SEQ ID NO:7; aa554 to aa561 of SEQ ID NO:7; aa555 to aa562 of SEQ ID NO:7; aa556 to aa563 of SEQ ID NO:7; aa557 to aa564 of SEQ ID NO:7; aa558 to aa565 of SEQ ID NO:7; aa559 to aa566 of SEQ ID NO:7; aa560 to aa567 of SEQ ID NO:7; aa561 to aa568 of SEQ ID NO:7; aa562 to aa569 of SEQ ID NO:7; aa563 to aa570 of SEQ ID NO:7; a64 to aa571 of SEQ ID NO:7; aa565 to aa572 of SEQ ID NO:7; aa566 to aa573 of SEQ ID NO:7; aa567 to aa574 of SEQ ID NO:7; aa568 to aa575 of SEQ ID NO:7; aa569 to aa576 of SEQ ID NO:7; aa570 to aa577 of SEQ ID NO:7; aa571 to aa578 of SEQ ID NO:7; aa572 to aa579 of SEQ ID NO:7; aa573 to aa580 of SEQ ID NO:7; aa574 to aa581 of SEQ ID NO:7; aa575 to aa582 of SEQ ID NO:7; aa576 to aa583 of SEQ ID NO:7; aa577 to aa584 of SEQ ID NO:7; aa578 to aa585 of SEQ ID NO:7; aa579 to aa586 of SEQ ID NO:7; aa580 to aa587 of SEQ ID NO:7; aa581 to aa588 of SEQ ID NO:7; aa582 to aa589 of SEQ ID NO:7; aa583 to aa590 of SEQ ID NO:7; aa584 to aa591 of SEQ ID NO:7; aa585 to aa592 of SEQ ID NO:7; aa586 to aa593 of SEQ ID NO:7;

aa587 to aa594 of SEQ ID NO:7; aa588 to aa595 of SEQ ID NO:7; aa589 to aa596 of SEQ ID NO:7; aa590 to aa597 of SEQ ID NO:7; aa591 to aa598 of SEQ ID NO:7; aa592 to aa599 of SEQ ID NO:7; aa593 to aa600 of SEQ ID NO:7; aa594 to aa601 of SEQ ID NO:7; aa595 to aa602 of SEQ ID NO:7; aa596 to aa603 of SEQ ID NO:7; aa597 to aa604 of SEQ ID NO:7; aa598 to aa605 of SEQ ID NO:7; aa599 to aa606 of SEQ ID N0:7; aa600 to aa607 of SEQ ID NO:7; aa601 to aa608 of SEQ ID NO:7; aa602 to aa609 of SEQ ID NO:7; aa603 to aa610 of SEQ ID N0:7; aa604 to aa611 of SEQ ID NO:7; aa605 to aa612 of SEQ ID NO:7; aa606 to aa613 of SEQ ID NO:7; aa607 to aa614 of SEQ ID NO:7; aa608 to aa615 of SEQ ID NO:7; aa609 to aa616 of SEQ ID NO:7; aa610 to aa617 of SEQ ID NO:7; aa611 to aa618 of SEQ ID NO:7; aa612 to aa619 of SEQ ID NO:7; aa613 to aa620 of SEQ ID NO:7; aa614 to aa621 of SEQ ID NO:7; aa615 to aa622 of SEQ ID NO:7; aa616 to aa623 of SEQ ID NO:7; aa617 to aa624 of SEQ ID NO:7; aa618 to aa625 of SEQ ID NO:7; aa619 to aa626 of SEQ ID NO:7. The coding sequence of fragments can be easily constructed by cleaving the unwanted nucleotides from the mutant or native DP-75 protein coding sequences.

Fusions are fragment, mutant, or native DP-75 proteins with additional amino acids at either or both of the termnini. The additional amino acid sequence is not necessarily homologous to sequence found in native hypothalmic receptor polypeptide. The additional amino acid residues can facilitate expression, detection, or activity of the polypeptide, for example. The additional amino acid sequence can also be used as linker to construct multimers of DP-75 proteins. All fusion polypeptide exhibit the desired sequence homology, immunological or biological activity.

As mentioned previously, recombinant DP-75 can be produced by prokaryotic microorganism or eukaryotic cells. Preferred cell systems include E. coli, mammalian, baculovirus, and yeast cells. Preferably, DP-75 is produced by transforming a prokaryotic microorganism with DNA to produce a protein that possesses native DP-75 activity.

Bacteria are prokaryotic microorganisms that may produce DP-75 and E. coli is especially preferred. Synthetic recombinant DP-75 can also be made in eukaryotes, such as yeast or human cells. See Sambrook, et al., MOLECULAR CLONING; A LABORATORY MANUAL, SECOND EDITION (1989), Volume 3, for bacterial expression, see chapter 17, for expression in mammalian cells, see chapter 16 both of which are hereby incorporated by reference.

DP-75 DNA can be incorporated into a bacterial expression vector which contains all the control sequences necessary for expressing DP-75 polypeptide. Control sequences are known in the art and include: a ribosome binding site, a regulated promoter (i.e. trp, trp-lac, $\lambda p_L$, and T7); optionally an operator sequence, an initiation (ATG) and stop codon; an enhancer, etc. It is also preferable to include a origin of replication to facilitate replication of the plasmid within the bacteria.

Appropriate vectors and plasmids are publicly available and can be employed to contain DP-75 DNA. It can be ligated, in operable linkage, to the above control sequences and inserted into the vector using commonly available ligation enzymes and techniques. Additionally, DP-75 DNA sequence can be inserted downstream of a sequence that provides for secretion into the periplasmic space, such as the phoA sequence.

A variety of bacterial hosts for expression are known in the art and available from the American Type Culture Collection (ATCC). Bacterial hosts suitable for expressing DP-75 include, without limitation: Campylobacter, Bacillus, Escherichia, Lactobacillus, Pseudomonas, Staphylococcus, and Streptococcus. A typical transformed microorganism useful in the present invention is E. coli K-12, strain MM294 (deposited with the American Type Culture Collection on Aug. 4, 1983, by Cetus Corporation under the provisions of the Budapest Treaty and assigned Accession No. 39,405).

Methods of introducing DP-75 DNA into bacterial hosts are well-known in the art, and typically include either treating the bacteria with $CaCl_2$ or other agents, such as divalent cations and DMSO. Naked or plasmid DNA can also be introduced into bacterial cells by electroporation or viral infection. Transformation procedures usually vary with the bacterial species to be transformed. See e.g., (Masson et al. (1989) FEMS Microbiol. Lett. 60:273; Palva et al. (1982) Proc. Natl. Acad. Sci. USA 79:5582; EP Publ. Nos. 036 259 and 063 953; PCT WO 84/04541, Bacillus), (Miller et aL (1988) Proc. Natl. Acad. Sci. 85:856; Wang et al. (1990) J. Bacteriol. 172:949, Campylobacter), (Cohen et al. (1973) Proc. Natl. Acad. Sci. 69:2110; Dower et al. (1988) Nucleic Acids Res. 16:6127; Kushner (1978) "An improved method for transformation of Escherichia coli with Co E1-derived plasmids in Genetic Engineering: Proceedings of the International Symposium on Genetic Engineering (eds. H. W. Boyer and S. Nicosia); Mandel et aL (1970) J. Mol. Biol. 53:159; Taketo (1988) Biochim. Biohvs. Acta 949:318; Escherichia), (Chassy et al. (1987) FEMS Microbiol. Lett. 44:173 Lactobacillus); (Fiedler et al. (1988) Anal. Biochem 170:38, Pseudomonas); (Augustin et al. (1990) FEMS Microbiol. Leti 66:203, Staphylococcus), (Barany et al. (1980) J. Bacteriol. 144:698; Harlander (1987) "Transformation of Streptococcus lactis by electroporation," in Stretococcal Genetics (ed. J. Ferretti and R. Curtiss III); Perry et al. (1981) Infec. Immun. 32:1295; Powell et al. (1988) Appl. Environ. Microbiol. 54:655; Soinkuti et aL (1987) Proc. 4th Evr. Cong. Biotechnology 1:412, Streptococcus).

Exemplary processes for growing, harvesting, disrupting, or extracting the DP-75 polypeptide from cells are substantially described in U.S. Pat. Nos. 4,604,377, 4,738,927, 4,656,132, 4,569,790, 4,748,234, 4,530,787, 4,572,298, 5,248,769, and 5,162,507, which are ereby incorporated by reference in their entireties.

DP-75 can be expressed in a variety of other expression systems; for example, referably mammalian or baculovirus expression systems, as well as yeast systems.

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter win also contain an upstream promoter element, usually located within 100 to 200 bp upstream of the TATA box. An upstream promoter element detemines the rate at which transcription is initiated and can act in either orientation, Sambrook et al., Molecular Cloning: A Laboratory Manual (2nd ed. 1989).

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter, Maniatis et al., Science 236:1237 (1989); Alberts et al. Molecular Biology of the Cell, 2nd ed (1989). Enhancer elements derived from viruses may be particularly useful, because they usually have a broader host range. Examples include the SV40 early gene enhancer, Dijkerna et al (1985) EMBO J. 4:761, and the enhancer/promoters derived from the long terminal repeat (LTR) of the Rous Sarcoma Virus, Gorman et al. (1982) Proc. Natl. Acad. Sci. 79:6777, and from human cytomegalovirus, Boshart el al. (1985) Cell 41:5221. Additionally, some enhancers are regulatable and become active only in the presence of an inducer, such as a hormone or metal ion, Sassone-Corsi et al. (1986) Trends Genet. 2:215; Maniatis et al. (1987) Science 236:1237.

A protein molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminal methionine may be cleaved from the protein by in vitro incubation with cyanogen bromide.

Alternatively, foreign proteins can also be secreted from the cell into the growth medium by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus tripartite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation, Birustiel et al. (1985) Cell 41:349; Proudfoot and Whitelaw (1988) "Termination and 3' end processing of eukaryotic RNA. In Transcription and splicing (ed. B. D. Hames and D. M. Glover); Proudfoot (1989) Trends Biochem. Sci. 14:105. These sequences direct the transcription of an mRNA which can be translated into the polypeptide encoded by the DNA. Examples of transcription terminator/polyadenylation signals include those derived from SV40, Sambrook et al (1989), Molecular Cloning: A Laboratory Manual.

Some genes may be expressed more efficiently when introns are present. Several cDNAs, however, have been efficiently expressed from vectors that lack splicing signals (also called splice donor and acceptor sites), see e.g., Gething and Sambrook (1981) Nature 293:620. Introns are intervening non coding sequences within a coding sequence that contain splice donor and acceptor sites. They are removed by splicing following polyadenylation of the primary transcript, Nevins (1983) Annu. Rev. Biochem. 52:441; Green (1986) Annu. Rev. Genet. 20:671; Padgett el al. (1986) Annu. Rev. Biochem. 5:1119; Krainer and Maniatis (1988) "RNA splicing," In Transcription and splicing (ed. B. D. Hames and D. M. Glover).

Usually, the above-described components, comprising a promoter, polyadenylation signal, and transcription termination sequence are put together into expression constructs. Enhancers, introns with functional splice donor and acceptor sites, and leader sequences may also be included in an expression construct, if desired. Mammalian replication systems include those derived from animal viruses, which require trans-acting factors to replicate. For example, plasmids containing the replication systems of papovaviruses, such as SV40, Gluztnan (1981) Cell 23:175, or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a prokaryotic host for cloning and amplification. Examples of such mammalian-bacteria shuttle vectors include pMT2, Kaufman et al (1989) Mol. Cell. Biol. 9:946, and pHEBO, Shimizu et al (1986) Mol. Cell. Biol. 6:1074.

The transformation procedure used depends upon the host to be transformed. Methods for introduction of heterologous polynucleotides into mammalian cells are known in the art and include dextran-mediated tansfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

The DP-75 nucleic acid sequence can also be inserted into a suitable insect expression vector, and is operably linked to the control elements within that vector. Vector construction employs techniques which are known in the art.

Generally, the components of the expression system include a transfer vector, usually a bacterial plasmid, which contains both a faent of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene into the baculovirus genome); and appropriate insect host cells and growth medium.

After inserting the DP-75 DNA sequence into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, Texas Agricultural Experiment Station Bulletin No. 1555 (1987) hereinafter "Summers and Smith").

Prior to inserting the DNA sequence encoding the protein into the baculovirus genome, the above-described components, comprising a promoter, leader (if desired), coding sequence of interest, and traiption termination sequence, are usually assembled into an intermediate construct (transfer vector).

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a Bamff cloning site 32 base pairs downstream from the ATT; see Luckow and Summers, *Virology* (1989) 17:31. The plasmid usually also contains the polyhedron polyadenylation signal (Miller et al. (1988) *Ann. Rev. Microbio,* 42:177) and a prokaryotic ampicillin-resistance (amp) gene and origin of replication for selection and propagation in *E. coli.*

Baculovirus transfer vectors usually contain a baculovirus promoter. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly usefull promoter sequences. Examples include sequences derived from the gene encoding the viral polyhedron protein, Friesen et al., (1986) "The Regulation of Baculovirus Gene Expression," in: The Molecular Biology of Baculoviruses (ed. Walter Doerfier); EPO Publ. Nos. 127 839 and 155 476; and the gene encoding the p10 protein, Vlak et aL, (1988), *J Gen Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et aL, (1987) *Gene* 58:273; and human glucocerebrosidase, Martin et al. (1988) *DNA* 7:99, can also be used to provide for secretion in insects.

After insertion of the DNA sequence and/or the gene encoding the expression product precursor of the protein, an insect cell host is co-tansformed with the heterologous DNA of the transfer vector and the genomic DNA of wild type baculovirus—usually by co-transfection. Methods for introducing heterologous DNA into the desired site in the baculovirus virus are known in the art. (See Summers and Smith; Ju et aL (1987); Smith et al., *Mol. Cell. Biol* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller el al., (1989), *Bioessays* 4:91.

The newly formed baculovirus expression vector is subsequently packaged into an infectious recombinant baculovirus. Methods to identify recombinant viruses are described in "Current Protocols in Microbiology" Vol. 2 (Ausubel et al. eds) at 16.8 (Supp. 10, 1990); Summers and Smith; Miller el aL (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodopterafrugiperda,* and *Trichoplusia ni* (PCT Pub. No. WO 89/046699; Carbonell et al., (1985) *J Virol.* 56:153; Wright (1986) *Nature* 321:718; Smith el al., (1983) *Mol. Cell. Biol.* 3:2156; and see generally, Fraser, et al. (1989) *In Vitro Cel. Dev. Biol.* 25:225).

Yeast expression systems are also known to one of ordinary skill in the art. Although less preferred in the present invention, such systems may be used. For a general review of yeast expression, see Barr et al. (eds.), Yeast Genetic Engineering, Butterworths, London (1989).

DP-75 protein may be purified after expression in a host cell system by a sequence of recovery and purification steps. For instance, DP-75 expressed as a soluble protein in *E. coli* may be released by breaking the bacterial cells in a microfluidizer and recovered by 30% ammonium sulfate precipitation. DP-75 protein may then be redissolved in buffer and purified by a variety of steps including, for example, anion exchange chromatography, size exclusion chromatography, hydroxyapatite chromatography, hydrophobic interaction chromatography, metal chelation chromatography, reverse phase HPLC, affinity chromatography, and further ammonium sulfate precipitations. These techniques are well known to those of skill in the art.

The DP-75 protein can be used in an assay for inhibitors and for preparing antibodies directed to DP-75. DP-75 protein may also be usefull as a factor that promotes the growth of cancer cells in culture. The DP-75 protein may be combined with the pharmaceutically acceptable carrier noted above for use with the DP-75 antisense molecule.

The present invention will now be illustrated by reference to the following examples which set forth particularly advantageous embodiments. However, it should be noted that these embodiments are illustrative and are not to be construed as restricting the invention in any way.

EXAMPLES

Example 1

Isolation of SEO ID NO:1 (MP-75)

The partial nucleic sequence for DP-75 is set forth below as SEQ ID NO: 1 as s single stranded molecule.

SEO ID NO:1
AAGGCCTTTGTTTGGGTGCCCGAAC-
CCCACCAAGCAGCATTCCTCACGCTGGAG
TCCTACCTCATCAAGCCGGTTCA-
GAGAGCGCTCAGGTACCCGCTGCTGCTCAAG
GAGCTGGTGTCCCTGACGGACCAG-
GAGAGCGGAGGAGCACTACCACCTGACGGA
AGCACTAAAGGCAATGGAGAAAGTAGC-
GAGCCACATCAATGAGATGCAGAAG ATCTATGAG-
GATTATGGGACCGTGTTGACCAGCTAG-
TAGCTGAGCAGAGCGG
AACAGAGAAGGAGGTAACAGAACTTTC-
GATGGGAGAGCTTCTGATGCACTCTA CGGTTTC-
CTGGTTGAACCCAATGTTGATCCCCGGGG

DP-75 was isolated from hypothalamic cDNA by constructing nucleic acid probes as follows. The first 19 nucleotides (AAGGCCTTTGTTGGGTGCC), (SEQ ID NO:2) come from degenerate oligo DO-3 (AAGGCCTTTGYTGGNYNCC) (SEQ ID NO:3) and the complement of the last 22 nucleotides (CCCCGGGGATCAACATTGGGTh (SEQ ID NO:4) come from degenerate oligo DO 14 (CCCCGGGGATVADVADDGGRTD (SEQ ID NO:5). The sequence AGGCCT of DO-3 comprises a StuI restriction site and the sequence CCCGGG of DO-14 comprises a SmaI restriction site. PCR was performed on hypothalamic cDNA and the resulting products were cloned and sequenced.

A library of human tissues was screened for the presence of DP-75. Commercially available northern blots were purchased from Clontech Laboratories Inc., 4030 Fabian Way, Palo Alto, Calif. One blot contained approximately 2 micrograms of poly A$^+$ RNA per lane from eight different human tissues. RNA was run on a denaturrg formaldehyde 1.2% agarose gel, transferred to a charge-modified nylon membrane by Northern blotting, and fixed by UV irradiation. Lanes 1–8 contained RNA from heart, brain, placenta, lung, liver, skeletal muscle, kidney, and pancreas. RNA size marker bands were indicated. A second blot contained 2 micrograms of poly A$^+$ RNA per lane from eight different brain sections. The blot was prepared as above. The brain sections were human cerebellum, cerebral cortex, medulla, spinal cord, occipital pole, frontal lobe, temporal lobe, and putamen. DP-75 was found to be expressed in normal heart, brain, and skeletal muscle.

The message size was mostly 3 Kb for brain, and appeared to be 6 Kb in heart and skeletal muscle. A more complete look at regions of the brain showed that the cerbral cortex, occipital pole, frontal lobe, temporal lobe and putamen contained a 3 Kb message, but that the cerebellum contained a 7.7 Kb message. Accordingly, it appears that there may be differentially spliced versions of DP-75 in various regions of the body.

Example 2

Utilizing SEO ID NO:1 to Diagnose Cancer

In a dot blot assay, DP-75 was hybridized to RNA from both cancerous and normal tissue. The source of cancerous tissue include renal, thyroid, breast, colon, ureter, lung, nose, stomach, esophagus, liver, lymphoma, uterus, bladder, rectum, and brain.

The blots were purchased from BioChain Institue, Inc., San Leandro, Calif., USA. ExpressHyb™ hybridization buffer, purchased from Clontech, Palo Alto, Calif., USA, was used for the blotting at 68° C. with DP-75 (SEQ IDNO:1) at 1×10$^6$ cpm/ml for 2 hours.

In four of four thyroid samples, SEQ ID NO:1 (DP-75) mRNA levels were higher in the cancer than the normal samples. See FIG. 1.

In two of the four colon samples, SEQ ID NO:1 (D)P-75) mRNA levels were higher in the cancer tan the normal samples. See FIG. 1.

In one of two ureter samples, the SEQ ID NO:1 (DP-75) mRNA level were higher in the cancer than the normal sample. See FIG. 1.

In one of four breast samples, the SEQ ID NO:l (DP-75) mRNA level were higher in the cancer than the normal sample. See FIG. 1.

In one of four renal sample, the SEQ ID NO:1 (DP-75) mRNA level were higher in the cancer than the normal sample. See FIG. 1.

In all other tissue types tested, the SEQ ID NO:l (DP-75) MnRNA levels were the same or higher in the normal samples than the cancer samples.

Example 3

Isolation of SEO ID NO:6

SEQ ID NO:6 was isolated from a frontal cortex library utilizing a phage vector, and was purchased from Stratagene, La Jolla, Calif., USA. The library was probed with SEQ ID NO: 1, which was generated by a random primed label with a final radioactive count of approximately 1×10$^6$ cpm/ml. The probe was labeled according to manufacturer's instruction with a RediPrimrea™ DNA labeling kit purchased from Amersham, Arlington Heights, Ill., USA.

The phage library was propagated and then plated onto twenty plates according to the manufacturer's instructions with a 3.0–5.0×10$^5$ plaques/plate. The plaques were transferred to a nitrocellulose membranes. Each membrane was incubated with the SEQ ID NO:1 probe for 2 hours at 65° C. in ExpressHyb™ hybridization solution purchased from Clontech, Palo Alto, Calif., USA. The filters were washed according to the Clontech instruction. Film was exposed to the membranes to identify putative positive plaques containing the desired DP-75 polynucleotide.

A second round of plating and hybridization was performed to identify a single positive plaque. The positive plaques from the first round were propagated and plated onto agar medium according to the instructions provided by Stratagene. The plaques were transferred to filters. These filters were incubated with the SEQ ID NO:1 probe. The probe and hybridization conditions were the same as described above. Positive plaques were identified and propagated.

According to the instructions provided by Stratagene, a BlueScript plasmid was rescued from the phage vector. The EcoRI insert from the plasmid was sequenced. The polynucleotide sequence is shown in SEQ ID NO:6.

Other DP-75 polypeptide coding sequences can be isolated using primer extension and PCR techniques to generate libraries. These techniques can utilize priners comprising SEQ ID NO:1 or SEQ ID NO:6 or mutants, fusions, or fragments thereof.

Once the libraries are generated, other DP-75 polynucleotides can be identified from the library using probes comprising a sequence from SEQ ID NO:l or SEQ ID NO:6 or mutant, fusion, or fragments thereof.

DP-75 polypeptide, polynucleotides, or antibodies can be administered orally, topically, or by parenteral means, including subcutaneous and intramuscular injection, implantation of sustained release depots, intravenous injection, intranasal administration, and the like. When used to treat tumors, it may be advantageous to apply the DP-75 polynucleotides or antibodies, for example, directly to the site, e.g., during surgery to remove the bulk of the tumor. Accordingly, DP-75 polypeptide, polynucleotides, or antibodies may be administered as a pharmaceutical composition comprising a pharmaceutically acceptable excipient Such compositions may be aqueous solutions, emulsions, creams, ointments, suspensions, gels, liposomal suspensions, and the like.

Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases usefull in formulation include lanolin, Silvadene® (Marion), Aquaphor® (Duke Laboratories), and the like. Other topical formulations include aerosols, bandages, and other wound dressings. Alternatively, one may incorporate or encapsulate the DP-75 polypeptide, polynucleotides, or antibodies in a suitable polymer matrix or membrane, thus providing a sustined-release delivery device suitable for implantation near the site to be treated locally. Other devices include indwelling catheters and devices such as the Alzet® minipump. Ophthalmic preparations may be formulated using commercially available vehicles such as Sorbi-care® (Allergan), Neodecadron® (Merck, Sharp & Dobine), Lacrilube®, and the like, or may employ topical preparations such as that described in U.S. Pat. No. 5,124,155, incorporated herein by reference. Further, one may provide a DP-75 polypeptide, polynucleotide, or antibody in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

The amount of DP-75 polypeptide, polynucleotide, or antibody required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples.

The present invention has been described with reference to specific embodiments. However, this application is intended to cover those changes and substitutions which may be made by those skilled in the art without departing from the spirit and the scope of the appended claims.

Deposit Information

The following materials were deposited with the American Type Culture Collection:

| Name | Deposit Date | Accession No. |
|---|---|---|
| *Escherichia coli* INVαF' DP 75 | 25 April 1996 | 98030 |

The above materials have been deposited with the American Type Culture Collection, Rockville, Md., under the accession numbers indicated. This deposit will be maintained under the terms of the Budapest Treaty on the International Recognition of the Deposit of Microorganisms for purposes of Patent Procedure. The deposits will be maintained for a period of 30 years following issuance of this patent, or for the enforceable life of the patent, whichever is greater. Upon issuance of the patent, the deposits will be available to the public from the ATCC without restriction.

These deposits are provided merely as convenience to those of skill in the art, and are not an admission that a deposit is required under 35 U.S.C. §112. The sequence of the polynucleotides contained within the deposited materials, as well as the amino acid sequence of the polypeptide encoded thereby, are incorporated herein by reference and are controlling in the event of any conflict with the written description of sequences herein. A license may be required to make, use, or sell the deposited materials, and no such license is granted hereby.

What is claimed:
1. An isolated polynucleotide consisting of the nucleotide sequence of SEQ ID NO: 1.

* * * * *